United States Patent
Gottlieb et al.

(10) Patent No.: US 10,478,102 B2
(45) Date of Patent: *Nov. 19, 2019

(54) NEEDLE PROTECTIVE DEVICE FOR SUBCUTANEOUS SENSORS

(71) Applicant: MEDTRONIC MINIMED, INC., Northridge, CA (US)

(72) Inventors: Rebecca K. Gottlieb, Culver City, CA (US); Rajiv Shah, Rancho Palos Verdes, CA (US); Katherine T. Wolfe, Dunwoody, GA (US); Eric Allan Larson, Simi Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,304

(22) Filed: Jun. 1, 2018

(65) Prior Publication Data
US 2018/0271422 A1    Sep. 27, 2018

Related U.S. Application Data

(60) Division of application No. 15/057,330, filed on Mar. 1, 2016, now Pat. No. 10,010,275, which is a
(Continued)

(51) Int. Cl.
*A61B 5/05*    (2006.01)
*A61B 5/145*    (2006.01)
(Continued)

(52) U.S. Cl.
CPC ........ *A61B 5/14532* (2013.01); *A61B 5/1473* (2013.01); *A61B 5/6849* (2013.01);
(Continued)

(58) Field of Classification Search
None
See application file for complete search history.

(56) References Cited

U.S. PATENT DOCUMENTS

| 4,433,072 A | 2/1984 | Pusineri et al. |
| 4,494,950 A | 1/1985 | Fischell |

(Continued)

FOREIGN PATENT DOCUMENTS

| EP | 1338295 A1 | 8/2003 |
| EP | 1 704 889 A1 | 9/2006 |

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner* — Michael R Bloch
(74) *Attorney, Agent, or Firm* — Pillsbury Winthrop Shaw Pittman LLP

(57) ABSTRACT

An introducer is provided for introducing a sensor into the body of a patient. The introducer connects to a sensor hub. When the sensor hub and introducer are connected, the introducer needle is exposed. When the sensor hub and introducer are disconnected, a needle cover and the needle move with respect to each other so that the needle cover substantially covers the needle, protecting a user from being injured by the needle.

10 Claims, 18 Drawing Sheets

Related U.S. Application Data continuation of application No. 12/154,935, filed on May 28, 2008, now Pat. No. 9,295,786.

(51) Int. Cl.

| | |
|---|---|
| *A61B 5/00* | (2006.01) |
| *A61M 5/158* | (2006.01) |
| *A61M 5/32* | (2006.01) |
| *A61M 25/06* | (2006.01) |
| *A61M 37/00* | (2006.01) |
| *A61B 5/1473* | (2006.01) |
| *A61B 17/34* | (2006.01) |

(52) U.S. Cl.
CPC ......... *A61B 17/3496* (2013.01); *A61M 5/158* (2013.01); *A61M 5/3243* (2013.01); *A61M 25/0612* (2013.01); *A61M 37/0069* (2013.01); *A61M 2005/1585* (2013.01); *A61M 2005/3247* (2013.01)

(56) References Cited

U.S. PATENT DOCUMENTS

| | | |
|---|---|---|
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,726 A | 3/1988 | Allen, III |
| 4,781,798 A | 11/1988 | Gough |
| 4,871,351 A | 10/1989 | Feingold |
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,165,407 A | 11/1992 | Wilson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,497,772 A | 3/1996 | Schulman et al. |
| 5,543,326 A | 8/1996 | Heller et al. |
| 5,562,631 A | 10/1996 | Bogert |
| 5,569,186 A | 10/1996 | Lord et al. |
| 5,586,553 A | 12/1996 | Halili et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,700,250 A * | 12/1997 | Erskine ............... A61M 5/3269 604/164.12 |
| 5,750,926 A | 5/1998 | Schulman et al. |
| 5,779,665 A | 7/1998 | Mastrototaro et al. |
| 5,791,344 A | 8/1998 | Schulman et al. |
| 5,904,708 A | 5/1999 | Goedeke |
| 5,917,346 A | 6/1999 | Gord et al. |
| 5,965,380 A | 10/1999 | Heller et al. |
| 5,972,199 A | 10/1999 | Heller et al. |
| 5,999,848 A | 12/1999 | Gord et al. |
| 5,999,849 A | 12/1999 | Gord et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,259,937 B1 | 7/2001 | Schulman et al. |
| 6,275,717 B1 | 8/2001 | Gross et al. |
| 6,329,161 B1 | 12/2001 | Heller et al. |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,520,938 B1 | 2/2003 | Funderburk et al. |
| 6,554,798 B1 | 4/2003 | Mann et al. |
| 6,558,320 B1 | 5/2003 | Causey, III et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 7,303,543 B1 | 12/2007 | Maule et al. |
| 2002/0082665 A1 | 6/2002 | Haller et al. |
| 2002/0161288 A1 | 10/2002 | Shin et al. |
| 2003/0078560 A1 | 4/2003 | Miller et al. |
| 2003/0088166 A1 | 5/2003 | Say et al. |
| 2003/0109775 A1 | 6/2003 | O'Neil et al. |
| 2003/0152823 A1 | 8/2003 | Heller et al. |
| 2003/0168338 A1 | 9/2003 | Gao et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2004/0133164 A1* | 7/2004 | Funderburk ........ A61B 5/14532 604/134 |
| 2004/0158207 A1 | 8/2004 | Hunn et al. |
| 2004/0204687 A1 | 10/2004 | Mogensen et al. |
| 2005/0214585 A1 | 9/2005 | Li et al. |
| 2006/0258929 A1 | 11/2006 | Goode et al. |
| 2007/0073129 A1 | 3/2007 | Shah et al. |
| 2007/0093754 A1 | 4/2007 | Mogensen et al. |
| 2007/0191772 A1 | 8/2007 | Wojcik |
| 2008/0242962 A1 | 10/2008 | Roesicke et al. |

FOREIGN PATENT DOCUMENTS

| | | |
|---|---|---|
| WO | WO 96/37246 A1 | 11/1996 |
| WO | WO 02/058537 A2 | 8/2002 |
| WO | WO 2004/103170 A1 | 12/2004 |

(56) References Cited

FOREIGN PATENT DOCUMENTS

| WO | WO 2006/061354 A1 | 6/2006 |
|---|---|---|
| WO | WO 2008/014791 A1 | 2/2008 |
| WO | WO 2008/022476 A1 | 2/2008 |
| WO | WO 2008/051920 A2 | 5/2008 |

OTHER PUBLICATIONS

Abel et al., "A Method for Evaluating in vivo the Functional Characteristics of Glucose Sensors," Biosensors, 1986, pp. 211-220, vol. 2.
Boguslavsky et al., "Applications of redox polymers in biosensors," Solid State Ionics, 1993, pp. 189-197, vol. 60.
Geise et al., "Electropolymerized 1,3-diaminobenzene for the construction of a 1-1'-dimethylferrocene mediated glucose biosensor,"Analytica Chim. Acta.,1993, pp. 467-473, v18.
Gernet et al., "A planar glucose enzyme electrode," Sensors and Actuators, 1989, pp. 537-540, vol. 17, Elsevier Sequoia, Netherlands.
Gernet et al., "Fabrication and Characterization of a Planar Electrochemical Cell and Its Applications as a Glucose Sensor," Sensors and Actuators, 1989, pp. 49-70, vol. 18.
Gorton et al., "Amperometric glucose sensors based on immobilized glucose-oxidizing enzymes and chemically modified electrodes," Analytica Chim Acta., 1991, pp. 43-54, v. 249.
Gorton et al., "Amperometric biosensors based on an apparent direct electron transfer between electrodes and immobilized peroxidases," Analyst, 1992, pp. 1235-1241, vol. 117.
Gough et al., "Two-Dimensional Enzyme Electrode Sensor for Glucose," Analytical Chemistry, 1985, pp. 2351-2357, vol. 57.
Gregg et al., "Redox polymer films containing enzymes," J. Phys. Chem., 1991, pp. 5970-5975.
Gregg et al., "Cross-Linked Redox Gels Containing Glucose Oxidase for Amperometric Biosensor Applications," Anal. Chem., 1990, pp. 258-263, vol. 62.
Heller et al., "Electrical Wiring of Redox Enzymes," Accounts of Chemical Research, 1990, pp. 128-134, vol. 23, No. 5.
Johnson et al., "In vivo evaluation of an electroenzymatic glucose sensor implanted in subcutaneous tissue," Biosensors & Bioelectronics, 1992, pp. 709-714, vol. 7.
Jonsson et al., "An Electrochemical Sensor for Hydrogen Peroxide Based on Peroxidase Adsorbed on a Spectrographic Graphite Electrode," Electroanalysts, 1989, pp. 465-468, v.1.
Kanapieniene et al., "Miniature glucose biosensor with extended linearity," Sensors and Actuators, 1992, pp. 37-40, vol. B, No. 10.
Kawamori et al., "Perfect Normalization of Excessive Glucagon Responses to Intravenous Arginine in Human Diabetes Mellitus With . . . ," Diabetes, 1980, pp. 762-765, vol. 29.
Kimura et al., "An immobilized Enzyme Membrane Fabrication Method using an Ink Jet Nozzle," Biosensors, 1988, pp. 41-52, vol. 4.
Koudelka et al., "In-vivio Behaviour of Hypodermically Implanted Microfabricated Glucose Sensors," Biosensors & Bioelectronics, 1991, pp. 31-36, vol. 6.
Mastrototaro et al., "An electroenzymatic glucose sensor fabricated on a flexible substrate," Sensors and Actuators, 1991, pp. 139-144, vol. 5.
McKean et al., "A Telemetry-Instrumentation System for Chronically Implanted Glucose and Oxygen Sensors," IEEE Transactions on Biomedical Eng., 1988, pp. 526-532, vol. 35, No. 7.
Monroe, "Novel implantable glucose sensors," ACL, 1989, pp. 8-16.
Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n. 2.
Nakamato et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. of NIDDM . . . , 1994, p. 353-358, No. 1057.
Shichiri et al., "An artificial endocrine pancreas—problems awaiting solutions for long term clinical applications of . . . ," Frontiers Med. Biol. Eng., 1991, pp. 283-292, v.3.
Shichiri et al., "Wearable Artificial Endocrine Pancreas with Needle-Type Glucose Sensor," The Lancet, 1982, pp. 1129-1131, vol. 2 (8308).
Shichiri et al., "Telemetry Glucose Monitoring Device with Needle-Type Glucose Sensor," Diabetes Care, May-Jun. 1986, pp. 298-301, vol. 9, No. 3.
Shichiri et al., "Normalization of the Paradoxic Secretion of Glucagen in Diabetics Who Were Controlled by the Artificial Beta Cell," Diabetes, 1979, pp. 272-275, vol. 28.
Shichiri et al., "Closed-Loop Glycemic Control with a Wearable Artificial Endocrine Pancreas," Diabetes, 1984, pp. 1200-1202, vol. 33.
Shichiri et al., "In Vivo Characteristics of Needle-Type Glucose Sensor," Hormone and Metabolic Research, 1988, pp. 17-20, vol. 20.
Shichiri et al., "A Needle-Type Glucose Sensor," Life Support Systems: The Journal of the European Society for Artificial Organs, 1984, pp. 7-9, vol. 2, supplement 1.
Shichiri et al., "The Wearable Artificial Endocrine Pancreas with a Needle-Type Glucose Sensor," Acta Pediatr, Jpn, 1984, pp. 358-370, vol. 26.
Shichiri et al., "Glycaemic Control in Pancreatectomized Dogs with a Wearable Artificial Endocrine Pancreas," Diabetologica, 1983, pp. 179-184, vol. 24.
Shichiri et al., "Membrane design for extending the long-life of an implantable glucose sensor," Diab. Nutr. Metab., 1989, pp. 309-313, vol. 2.
Shinkai et al., "Molecular Recognition of Mono- and Di-Saccharides by Phenylboronic Acids in Solvent Extraction and as a Monolayer," J. Chem. Soc., 1991, pp. 1039-1041.
Tamiya et al., "Micro Glucose Sensors Using Electron Mediators Immobilized on a Polypyrrole-Modified Electrode," Sensors and Actuators, 1989, pp. 297-307, v.18.
Tsukagoshi et al., "Specific Complexation with Mono- and Disaccharides That Can Be Detected by Circular Dichroism," J. Org. Chem., 1991, pp. 4089-4091, vol. 56.
Urban et al., "Minaturized multi-enzyme biosensors integrated with pH sensors on flexible polymer carriers . . . ," Biosensors & Bioelectronics, 1992, pp. 733-739, vol. 7.
Urban et al., "Miniaturized thin-film biosensors using covalently immobilized glucose oxidase," Biosensors & Bioelectronics, 1991, pp. 555-562, vol. 6.
Velho et al., "In vivo calibration of a subcutaneous glucose sensor for determination of subcutaneous glucose kinetics," Diab. Nutr. Metab., 1988 pp. 227-233, v.3.
Yokoyama et al., "Integrated Biosensor for Glucose and Galactose," Analytica Chimica Acta., 1989, pp. 137-142, vol. 218.
Nishida et al., "Development of a ferrocene-mediated needle-type glucose sensor . . . ," Medical Process Through Technology, 1995, pp. 91-103, vol. 21.
Koudelka et al., "Planar Amperometric Enzyme-Based Glucose Microelectrode," Sensors and Actuators, 1989, pp. 157-165, vol. 18.
Yamasaki et al., "Direct measurement of whole blood glucose by a needle-type sensor," Clinica Chimica Acta., 1989, pp. 93-98, vol. 93.
Sternberg et al., "Study and Development of Multilayer Needle-type Enzyme-based Glucose Microsensors," Biosensors, 1988, pp. 27-40, vol. 4.
Shaw et al., "In vitro testing of a simply constructed, highly stable glucose sensor suitable for implantation . . . ," Biosensors & Bioelectronics, 1991, pp. 401-406, vol. 6.
Poitout et al., "A glucose monitoring system for on line estimation in man of blood glucose concentration using a miniaturized . . . ," Diabetologia, 1993, pp. 658-663, vol. 36.
Hashigushi et al., "Development of a Miniaturized Glucose Monitoring System by Combining a Needle-Type Glucose Sensor . . . ," Diabetes Care, 1994, pp. 387-389, v.17, n.5.

(56) References Cited

OTHER PUBLICATIONS

Jobst et al., "Thin-Film Microbiosensors for Glucose-Lactate Monitoring," Anal. Chem., 1996, p. 3173-79, vol. 68.
Shults et al., "A Telemetry-Instrumentation System for Monitoring Multiple Subcutaneously Implanted Glucose Sensors," IEEE Trans. on Biomed. Eng., 1994, pp. 937-942, v41, n.10.
Wang et al., "Needle-Type Dual Microsensor for the Simultaneous Monitoring of Glucose and Insulin," Anal. Chem., 2001, pp. 844-847, vol. 73.
Moussey et al., "Performance of Subcutaneously Implanted Needle-Type Glucose Sensors Employing a Novel Trilayer Coating," Anal. Chem., 1993, 2072-77, vol. 65.
Bindra et al., "Design and In Vitro Studies of a Needle-Type Glucose Sensor for Subcutaneous Monitoring," Anal. Chem., 1991, pp. 1692-1696, vol. 63.
Invitation to Pay Additional Fees and, Where Applicable, Protest Fee and Partial International Search, (PCT/US2009/002945) (4-pgs).
International Search Report and Written Opinion of the International Searching Authority (PCT/US2009/002945) (18-pgs).

\* cited by examiner

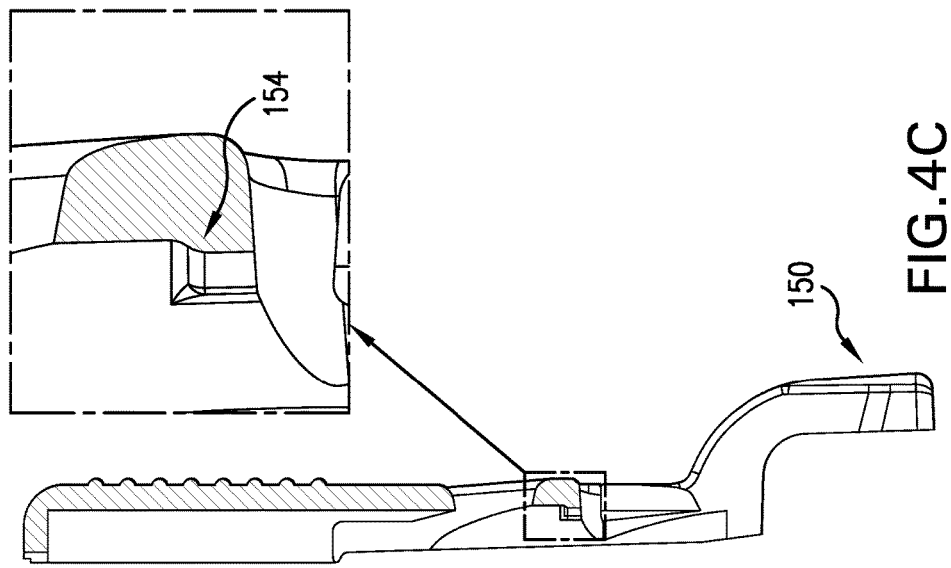
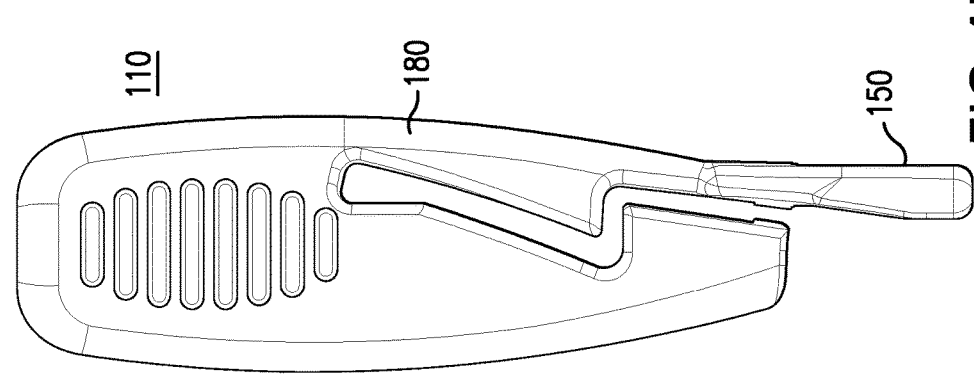
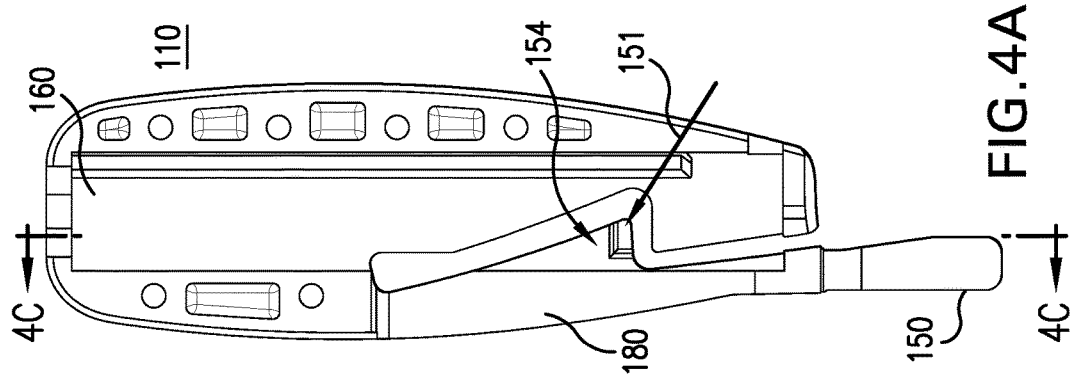
FIG. 4C
FIG. 4B
FIG. 4A

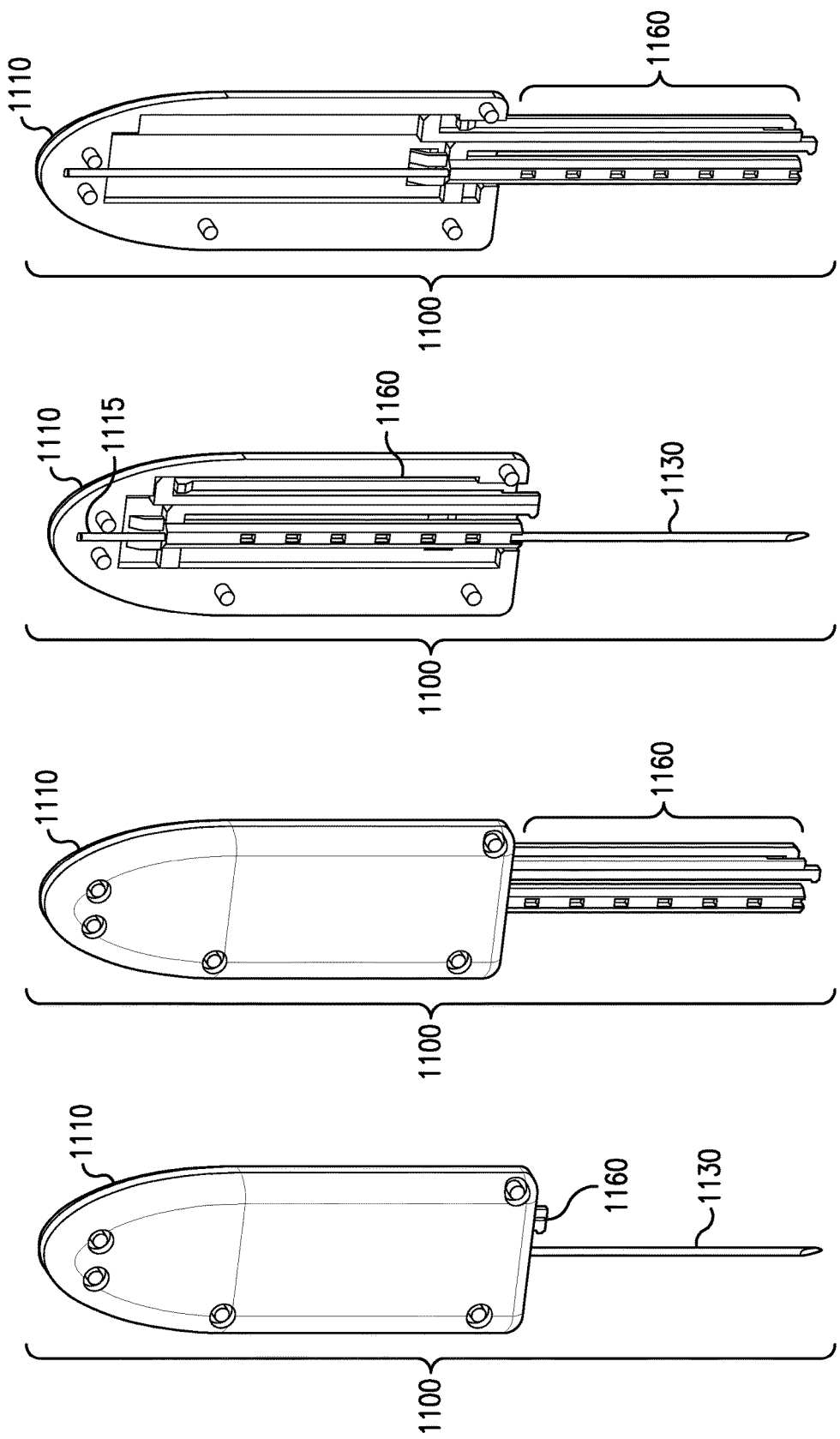

NEEDLE PROTECTIVE DEVICE FOR SUBCUTANEOUS SENSORS

RELATED APPLICATION DATA

This is a division of U.S. patent application Ser. No. 15/057,330, filed Mar. 1, 2016, now U.S. Pat. No. 10,010,275, which is a continuation of U.S. patent application Ser. No. 12/154,935, filed May 28, 2008, now U.S. Pat. No. 9,295,786, all of which are incorporated herein by reference in their entirety.

FIELD OF THE INVENTION

Field of the Invention

This invention relates generally to devices and methods for protecting users from needles used to insert subcutaneous sensors. More specifically, this invention relates to an introducer for a subcutaneous sensor including a needle cover that is operable to move in relation to a needle such that the needle cover covers the needle when the user is done using the introducer to insert the sensor.

Description of Related Art

Sensors are generally known in the art for use in a variety of specialized sensor applications. For example, thin film electrochemical sensors have been used to test analyte levels in patients. Such thin film sensors generally comprise one or more thin conductors applied by photolithography mask and etch techniques between thin layers of a nonconductive film material, such as polyimide film. The conductors are shaped to define distal segment ends having an appropriate electrode material thereon, in combination with proximal end contact pads adapted for conductive connection with appropriate electronic monitoring equipment. In recent years, thin film sensors of this general type have been proposed for use as a transcutaneous sensor in medical applications. As one example, thin film sensors have been designed for use in obtaining an indication of blood glucose ("BG") levels and monitoring BG levels in a diabetic patient, with the distal segment portion of the electrodes positioned subcutaneously in direct contact with patient extracellular fluid. Such readings can be especially useful in adjusting a treatment regimen which typically includes regular administration of insulin to the patient. In this regard, BG readings are particularly useful in conjunction with semi-automated medication infusion pumps of the external type, as generally described in U.S. Pat. Nos. 4,562,751; 4,678,408; and 4,685,903, and commonly assigned U.S. patent application Ser. No. 11/225,359, filed on Sep. 13, 2005, which are herein incorporated by reference; or automated implantable medication infusion pumps, as generally described in U.S. Pat. No. 4,573,994, which is herein incorporated by reference.

Relatively small and flexible electrochemical sensors have been developed for subcutaneous placement of sensor electrodes in direct contact with patient extracellular fluid, wherein such sensors can be used to obtain periodic readings over an extended period of time. Improved thin film sensors and related insertion sets are described in commonly assigned U.S. Pat. Nos. 5,390,671; 5,391,250; 5,482,473; 5,568,806; and 5,586,553 and International Publication No. WO 2004/036183, which are herein incorporated by reference, and commonly assigned pending U.S. patent application Ser. No. 11/234,722, filed Sep. 23, 2005, Ser. No. 11/234,523, filed Sep. 23, 2005, and Ser. No. 11/634,728, filed Dec. 6, 2006, which are herein incorporated by reference. See also U.S. Pat. No. 5,299,571, which is herein incorporated by reference.

Thin film sensors are often implanted subcutaneously/transcutaneously using an introducer tool. The introducer contains a needle that is used to puncture the skin of a patient at the same time as the sensor is introduced. The needle is then withdrawn, leaving the sensor in the skin of the patient. A thin film sensor can be placed on a cannula for ease of insertion. When using a cannula, the needle can be placed inside the cannula for insertion. Alternatively, a hollow needle can be used that surrounds the sensor (with or without a cannula).

The introducer, or insertion device, commonly including a needle, is used and then discarded after inserting the sensor at the sensor site. Therefore, upon withdrawal of the introducer, there are potential risks of unintended harm from the exposed end of the needle.

BRIEF SUMMARY OF THE INVENTION

The present invention relates to an improved introducer adapted to provide protection to a user after using the introducer to insert a sensor. The sensor may be an electrochemical sensor, such as a sensor that senses an analyte of a patient. For example, the sensor may sense the glucose level of a patient, such as a diabetic patient. The introducer could also be used to introduce other devices, such as the cannula of an infusion set for infusing a substance, such as insulin, to a patient.

In accordance with embodiments, an introducer is provided that includes a housing detachably connectable to a sensor hub containing a sensor, the housing includes a needle cover and a needle contained in and extending out of the housing, and the needle cover is operable to move in relation to the needle such that the needle cover covers the needle when the housing is detached from the sensor hub. Also provided are a sensor set including the introducer and a sensor hub and a method of covering a needle using the introducer.

In certain embodiments, the needle cover is an internal compartment of the housing. In further embodiments the introducer further comprises a needle holder connected to the needle and contained within the housing, where when the housing is connected to the sensor hub, the needle holder is in a needle extended position and the needle extends out of the housing, and when the housing is disconnected from the sensor hub, the needle holder moves in the housing to a needle covered position such that the needle is covered by the needle cover.

In certain embodiments, the needle holder is slidably coupled to the housing. In further embodiments, the introducer includes a spring connected to the needle holder, wherein when the housing is connected to the sensor hub, the spring is in a compressed position, and when the housing is disconnected from the sensor hub, the spring expands to move the needle holder in the housing such that the needle is covered by the housing.

In certain embodiments, the housing includes a mating component to mate with the sensor hub and hold the spring in a compressed position when the housing is connected to the sensor hub. In further embodiments, when the housing is disconnected from the sensor hub, the mating component releases the needle holder such that the needle holder may move into the needle covered position. In further embodiments, the mating component includes one or more locks that lock the needle holder into the needle extended position when the housing is connected to the sensor hub. In further embodiments, the one or more locks release the needle holder when the housing is disconnected from the sensor hub. The mating component may be held in a locking position by friction when the housing is connected to the sensor hub. It may include a catch that catches on the sensor hub when the housing is connected to the sensor hub, so that the mating component is held in a locking position by the catch.

In certain embodiments, the needle is permanently covered by the needle cover after the housing is disconnected from the sensor hub. In these embodiments, the needle is securely covered by the needle cover so that a user is protected from the needle. Preferably, after covering the needle, the needle would not be able to be uncovered from the needle cover without excessive force or breaking apart the introducer. In further embodiments, the needle may be partially covered such that the tip of the needle is covered so a user cannot prick himself with the needle. In still further embodiments, the needle cover may be a temporary cover such that a user can remove the cover without having to use excessive force or damage the introducer.

In certain embodiments, the introducer and its housing are composed of a substantially rigid plastic. The introducer may be made from a suitable plastics material that is substantially rigid but will allow it to flex and bend, such as polypropylene. However, the introducer may also be made out of a non-flexible material, such as polycarbonate, if preferred. Alternatively, the introducer may be made out of any suitable flexible or non-flexible material such as polyethylene, polyurethane, polyvinyl chloride, resins, polymers, ceramics, composites, or the like. For example, the material may be acrylonitrile butadiene styrene (ABS).

In certain embodiments, the needle cover is contained at least partially within the housing and is extendable over the needle and out of the housing. In further embodiments, when the housing is connected to the sensor hub, the needle cover is substantially contained within the housing, and when the housing is disconnected from the sensor hub, the needle cover extends over the needle, whereby the needle is covered by the needle cover. In further embodiments, the needle cover includes a needle cover catch operable to catch onto the sensor hub and extend the needle cover out of the housing when the sensor hub is separated from the housing.

In certain embodiments, the needle cover includes a locking element operable to lock the needle cover catch onto the sensor hub until the needle cover is substantially fully extended out of the housing. The locking element may move in the opposite direction from the sensor hub when the needle cover is substantially fully extended out of the housing, allowing the needle cover catch to uncatch from the sensor hub. In further embodiments, the housing includes an internal locking ledge and the locking element includes a locking element catch that catches on the internal locking ledge when the needle cover is substantially fully extended out of the housing, causing the locking element to move in the opposite direction from the sensor hub.

In certain embodiments, the needle cover includes one or more cover locks operable to lock the needle cover in an extended position. In further embodiments, the housing includes a locking opening and the one or more cover locks interact with the locking opening such that the needle cover is locked in an extended position.

In certain embodiments, a sensor set is provided with an introducer and a sensor hub, wherein when the introducer is connected to the sensor hub in a pre-insertion position, the needle is hidden in the sensor hub. In further embodiments, when the introducer is connected to the sensor hub in an insertion position, the needle extends out of the hub. For example, a pre-insertion position may be a position that the introducer and sensor hub are in prior to introducing a sensor into a patient. The user then moves the introducer and sensor hub into an insertion position, for example when the sensor hub is on the skin of the patient, so that the needle is inserted into the patient.

In certain embodiments, a sensor set is provided that includes a sensor hub including a sensor, a sensor electronics hub connectable to the sensor and including sensor electronics operable to receive signals from the sensor, a mounting base containing a first side and a second side, wherein the first side is attached at a first base portion to the sensor hub and is operable to mate with the sensor electronics hub at a second base portion. The sensor set may also include an introducer according to any of the embodiments described herein. In further embodiments, the sensor set includes a reusable adhesive attached to the second base portion on the first side of the mounting base, wherein the reusable adhesive is operable to removably adhere to the sensor electronics hub when the sensor electronics hub mates with the second base portion. In further embodiments, the sensor electronics hub has a top and a bottom and the second base portion includes an mounting extension configured to extend to the top of the sensor electronics hub, and wherein the reusable adhesive is attached to the second base portion at the mounting extension. The second base portion may include at least one additional mounting extension that also includes a reusable adhesive that is operable to removably adhere to the sensor electronics hub. In further embodiments, the second base portion includes a pocket that fits around at least a portion of the sensor electronics hub, and the reusable adhesive is attached to the second base portion in the pocket. When the sensor electronics hub is adhered to the reusable adhesive, it may be substantially stationary with respect to the second base portion. In this way, the sensor electronics hub will not wiggle in any great way or pull away from the mounting base, and the user will feel more comfortable knowing that it will be less likely to break away from the sensor hub. The sensor electronics hub may include a wireless transmitter. It may be directly connected or indirectly connected (e.g., by wire or other means) to the sensor hub. The mounting base may be flexible. If the mounting base is flexible, it can shape to the curvature of a patient's skin. The mounting base may further include an adhesive layer on the second side of the base, the adhesive layer being operable to adhere to the skin of a patient. In further embodiments, the mounting base is shaped to be of substantially the same shape as the bottom of the sensor hub and sensor electronics hub when the sensor hub is connected to the sensor electronics hub. The sensor electronics may include a wireless transmitter, which may be including in a transceiver, and the wireless transmitter may be adapted to transmit data to another device, such as a computer, user interface and/or drug delivery device (e.g., an insulin infusion device). Alternatively or additionally, the sensor electronics may include ways of wireless transmission of data.

In certain embodiments, a sensor hub is provided that includes a housing including a sensor carrier and a base, the base having a pocket, a sensor carried in the sensor carrier and extending into the carrier pocket, wherein the sensor carrier is operable to slide into the pocket such that the sensor extends out of the pocket and base. In further embodiments, the sensor hub includes a guide to guide the sensor carrier into the pocket. The guide may be part of or a separate component from the rest of the sensor hub. In still further embodiments, the sensor hub is part of a sensor set also including an introducer including a housing and a needle connected to and extending out of the housing, wherein the introducer is connected to the sensor hub at the sensor carrier such that the needle extends into the carrier pocket at least partially past the sensor, and wherein the carrier is operable to move into the pocket such that the needle and sensor extend out of the pocket and base.

Other features and advantages of the present invention will become more apparent from the following detailed description, taken in conjunction with the accompanying drawings which illustrate, by way of example, the principles of the invention.

BRIEF DESCRIPTION OF THE DRAWINGS

A detailed description of embodiments of the invention will be made with reference to the accompanying drawings, wherein like numerals designate corresponding parts in the figures.

FIGS. 4A-4C are views of an introducer in accordance with an embodiment of the invention.

FIGS. 9A and 9B are views of an introducer in accordance with an embodiment of the present invention.

FIGS. 10A and 10B are cut-away views of an introducer in accordance with an embodiment of the present invention.

DETAILED DESCRIPTION OF THE INVENTION

Figure 1:
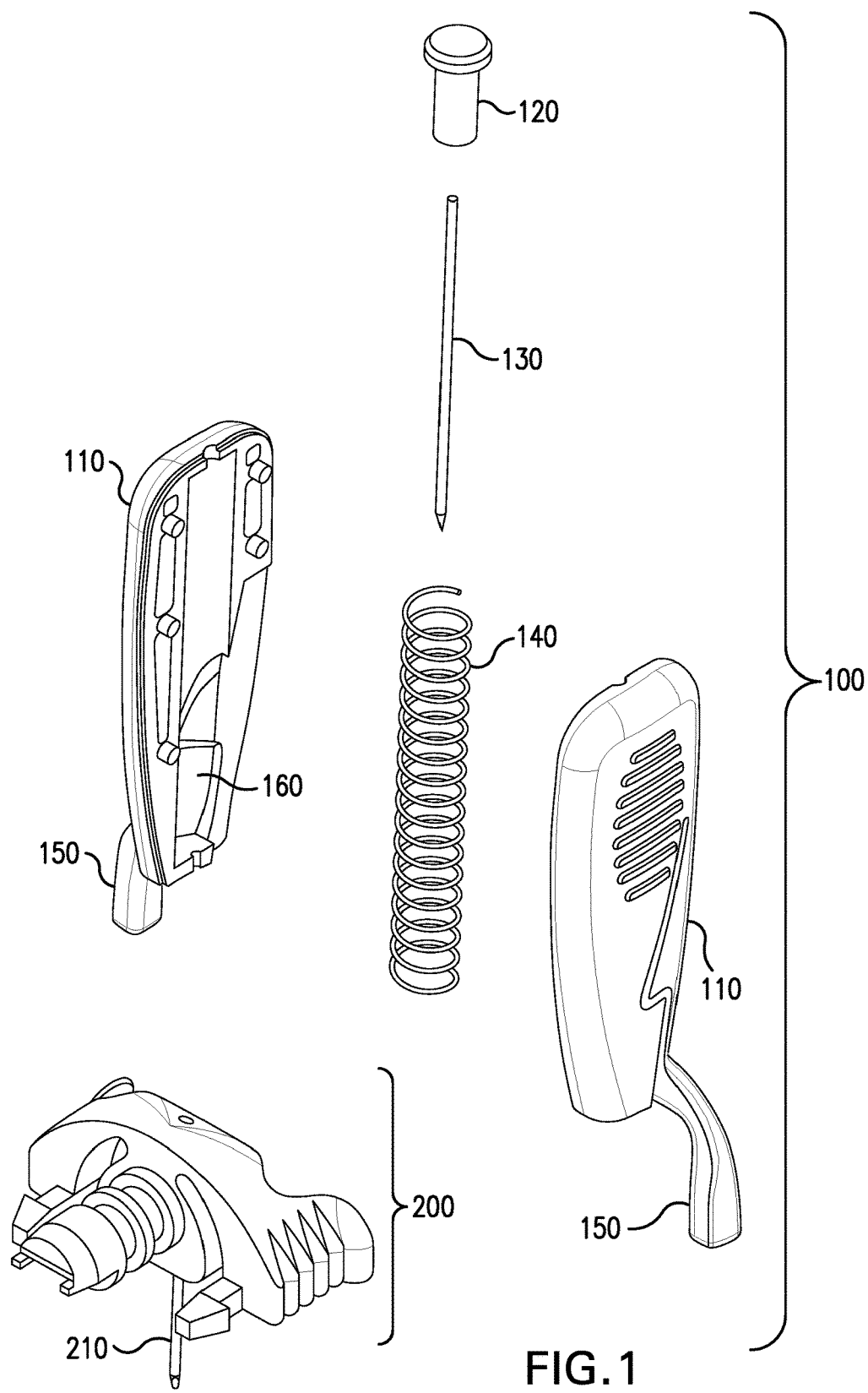
FIG. 1 is an expanded view of an introducer and sensor hub in accordance with an embodiment of the invention.

In the following description, reference is made to the accompanying drawings which form a part hereof and which illustrate several embodiments of the present inventions. It is understood that other embodiments may be utilized and structural and operational changes may be made without departing from the scope of the present inventions.

In embodiments of the present invention, an introducer is provided to introduce a sensor into a patient, such as a sensor that is part of a sensor hub. Alternatively, the introducer of the present invention can be used to introduce any other type of device that is introduced by use of a needle, for example, the cannula of an infusion set, such as an infusion set to infuse insulin into the body of a patient. In further alternative embodiments, the introducer may be utilized with combination sets that include a sensor and an infusion cannula, such as described in U.S. patent application Ser. No. 11/897,106 filed Aug. 29, 2007 entitled "Combined Sensor and Infusion Set Using Separated Sites"; and U.S. patent application Ser. No. 11/149,119 filed Jun. 8, 2005 entitled "Dual Insertion Set," both of which are herein incorporated by reference. The needle of the introducer is preferably covered after using the introducer for insertion, thus reducing risk of harm to the user. In embodiments discussed herein, the needle is automatically covered when the introducer is disconnected from a sensor hub.

The sensors implanted by the introducer may be used, for example, in subcutaneous or transcutaneous monitoring of analytes in a patient. For example, they may be used for monitoring of blood glucose levels in a diabetic patient. The sensors of the invention may also be used for sensing other analytes, such as lactate. While certain embodiments of the invention pertain to glucose sensors, the structure of the sensor disclosed and methods of creating the sensor can be adapted for use with any one of the wide variety of sensors known in the art. A number of enzyme sensors (e.g., glucose sensors that use the enzyme glucose oxidase to effect a reaction of glucose and oxygen) and related insertion sets are known. See, for example, U.S. Pat. Nos. 5,165,407, 4,890,620, 5,390,671, 5,299,571, 5,391,250, 5,482,473, 5,568,806, and 5,586,553, and International Publication No. WO 2004/036183, which are herein incorporated by reference. Sensors for monitoring glucose concentration of diabetics are further described in Schichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al., "In Vivo Measurement of Subcutaneous Glucose Concentrations with an Enzymatic Glucose Sensor and a Wick Method," Klin. Wochenschr. 67:491-495 (1989); and Pickup, et al., "In Vivo Molecular Sensing in Diabetes Mellitus: An Implantable Glucose Sensor with direct Electron Transfer," Diabetologia 32:213-217 (1989), which are herein incorporated by reference. Other sensors are described, for example, in Reach, et al., ADVANCES IN IMPLANTABLE DEVICES, A. Turner (ed.), JAI Press, London, Chap. 1, (1993), which is herein incorporated by reference. See also, commonly assigned U.S. patent application Ser. No. 11/234,523, filed on Sep. 23, 2005, and Ser. No. 11/234,722, filed on Sep. 23, 2005, which are herein incorporated by reference.

Infusion sets are typically used for delivering a selected medication or other fluid to a patient. Infusion sets may include a cannula, which may be relatively soft and flexible. The cannula provides a transcutaneous passageway to administer a medication or other fluid to a subcutaneous site on a patient. The cannula generally attached to a cannula housing/hub, which may be placed on the skin of the patient when the cannula is inserted. A connector attaches to the cannula housing/hub to connect the cannula to the fluid delivery system. The fluid delivery system is generally placed in fluid communication with the connector by way of a length of infusion tubing. Examples of fluid delivery systems are shown in U.S. Pat. Nos. 4,562,751, 4,685,903, 5,080,653, 5,097,122, 5,522,803, 5,561,886, 6,302,866, 6,485,465 and U.S. patent application Ser. No. 11/225,359, filed Sep. 13, 2005, and Ser. No. 11/644,526, filed Dec. 22, 2006, all of which are herein incorporated by reference.

As shown in FIG. 1 in an expanded view, in one embodiment of the invention, an introducer 100 is provided that can introduce a sensor 210 which is included in a sensor hub 200. The sensor hub 200 shown here can also be a cannula hub (or cannula housing) with a cannula for introducing a medication or therapeutic fluid such as insulin into a patient. The structure of the cannula hub may be similar to that of the sensor hub except that the sensor is replaced by the cannula. The cannula hub is a portion of an infusion set that includes the cannula hub and a connector to connect to an infusion pump. The introducer includes a housing 110, a needle holder 120, a needle 130, a spring 140, mating components 150 and a needle cover 160. The needle cover 160 is an internal compartment of the housing 110. The needle cover 160 is preferably contained within the housing and can move between a needle extended position, where the needle 130 is extended out of the housing 110, and a needle covered position, where the needle 130 is covered by the needle cover 160, within the housing 110. The introducer 100 connects to the sensor hub 200 before introducing the sensor 210 into the body of a patient. The introducer and sensor hub can be pre-connected as part of a sensor set, which could also include a sensor electronics hub that would connect to the sensor hub after insertion of the sensor in the body of the patient. Alternatively, the introducer and sensor hub could be a set or the introducer could be packaged and sold alone.

Figure 2A:
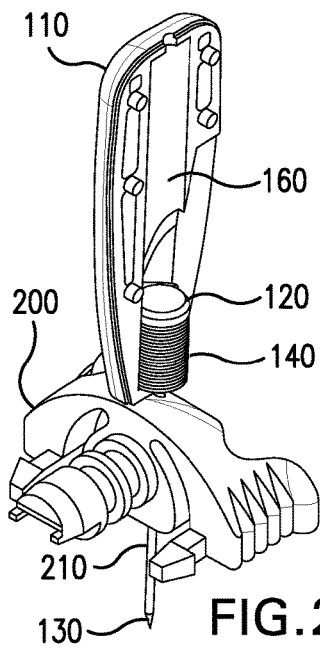
FIG. 2A is a partial view of an introducer and sensor hub in accordance with an embodiment of the invention.
Figure 3A:
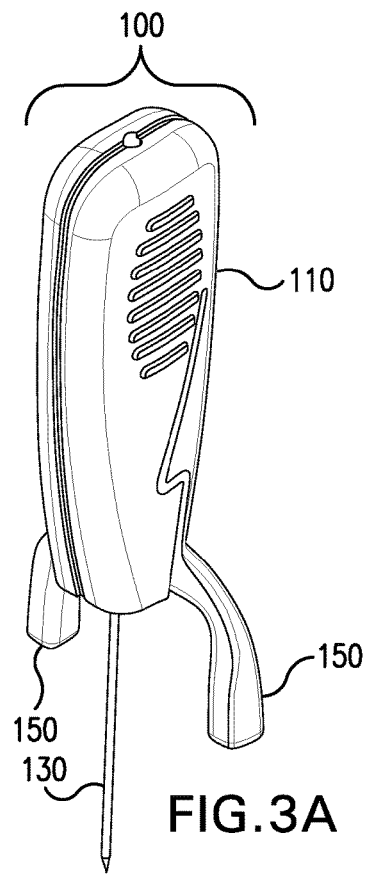
FIGS. 3A and 3B are views of an introducer in accordance with an embodiment of the invention.

FIG. 2A shows a cut-away view of an introducer 100 and sensor hub 200 prior to using the introducer 100 to introducer the sensor 210 into the body of a patient. As can be seen, the needle 130 extends beyond the sensor 210, so that it can create a hole in the skin of the patient into which the sensor 210 can enter. The needle holder 120 is in a needle extended position, toward the base of the introducer 100, in the housing 110. The needle holder 120 is coupled to the spring 140. The spring 140 is in a compressed position. FIG. 3A shows the exterior of the introducer 100 prior to introducing the sensor (not shown). The sensor hub is not shown in FIG. 3A, but as discussed herein, in preferred embodiments, the needle 130 is extended when the sensor hub is connected to the introducer 100.

Figure 2B:
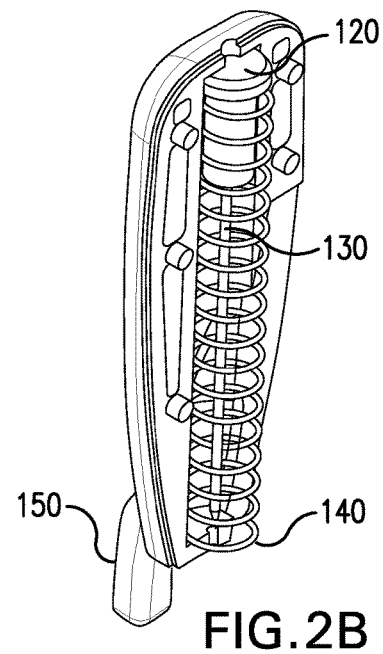
FIG. 2B is a partial view of an introducer in accordance with an embodiment of the invention.
Figure 3B:
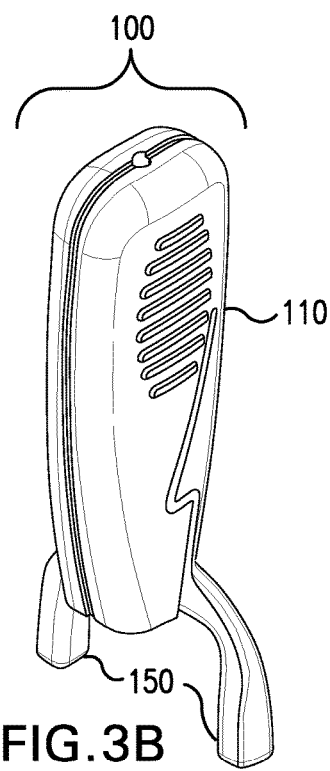

After introducing the sensor into the body of a patient, the user disconnects the sensor hub 200 from the introducer 100. When the sensor hub 200 is disconnected from the introducer 100, the needle holder moves into a needle covered position as shown in FIG. 2B. The spring 140 expands, pushing the needle holder 120 in the housing 110 to the needle covered position, nearer to the top of the housing 110. Another method of moving the needle holder in the housing could alternatively be used. This movement may be a sliding movement. The needle 130 is preferably attached to the needle holder 120 so that when the needle holder 120 moves to the needle covered position, the needle 130 moves into the needle cover 160 so that the needle 130 is covered by the needle cover 160. The needle 130 is preferably completely covered. In alternative embodiments, the needle 130 is not completely covered, but the tip is covered such that it cannot injure someone holding the introducer. The needle 130 is preferably permanently covered after being used so that it cannot be uncovered accidentally without undue force, such as breaking apart the introducer. In alternative embodiments, the covering of the needle is temporary. FIG. 3B shows the exterior of the introducer 100 after the needle has been covered by the needle cover in the housing 110. The needle is thus hidden by the needle cover.

FIGS. 4A-C show side views of the introducer 100. FIG. 4A shows the interior of one side of housing 110 of the introducer 100. The mating component 150 comprises some or all of an arm 180 of the housing 110. The needle cover 160 is an internal cavity of the housing 110. The embodiment shown in FIGS. 4A-C shows one of two mating components or mating elements 150. In FIG. 4A, the mating component 150 curves into the page. In FIG. 4B, the mating component 150 curves out of the page. A corresponding mating component 150 is part of the other half of the introducer 100 and extends in the opposite direction, as shown in FIGS. 1-3, for example. In other embodiments one mating component may be used or more than two mating components may be used. Preferably, at least two mating components are used to improve locking of the needle holder at the needle extended position within the housing. The mating component 150 includes one or more locks 154 that lock the needle holder at the needle extended position. As shown in FIG. 4A, the application of force on the arm 180 is in the direction of arrow 151. When force is applied to the arm 180, it causes it to bend throughout its length, but mostly at the top. When this happens, the lock 154 (and corresponding lock on the other arm) interferes with the needle holder. FIG. 4C shows a cut-away view of the introducer 100 along the line of A-A from FIG. 4A. It also shows a close-up view of one of the locks 154.

Figure 5A:
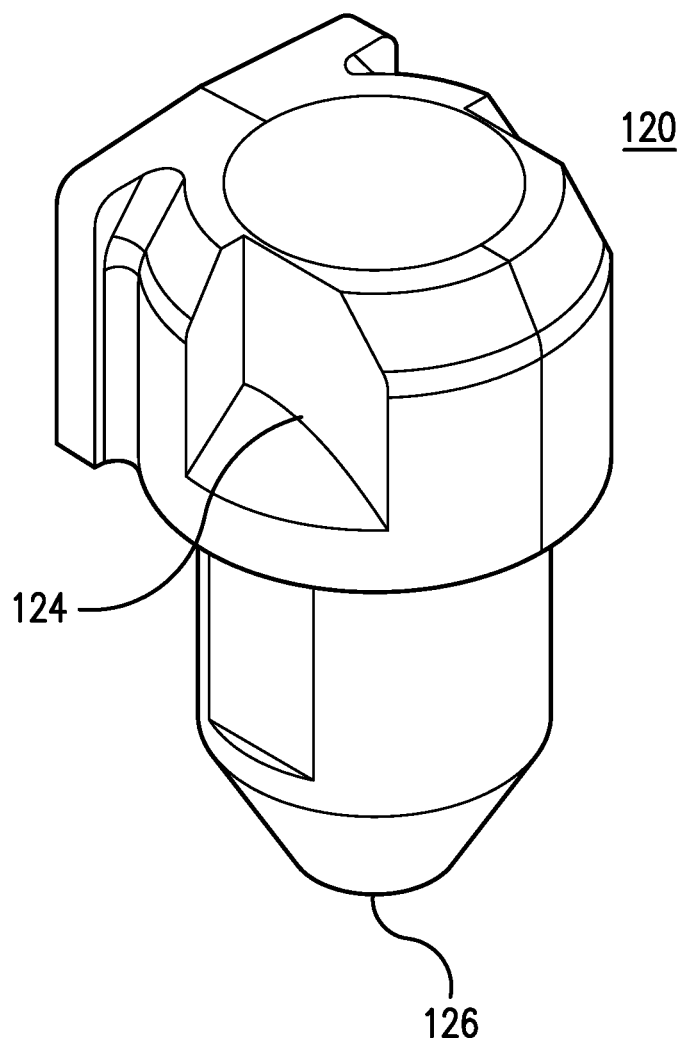
FIG. 5A is a view of a needle holder in accordance with an embodiment of the invention.
Figure 5B:
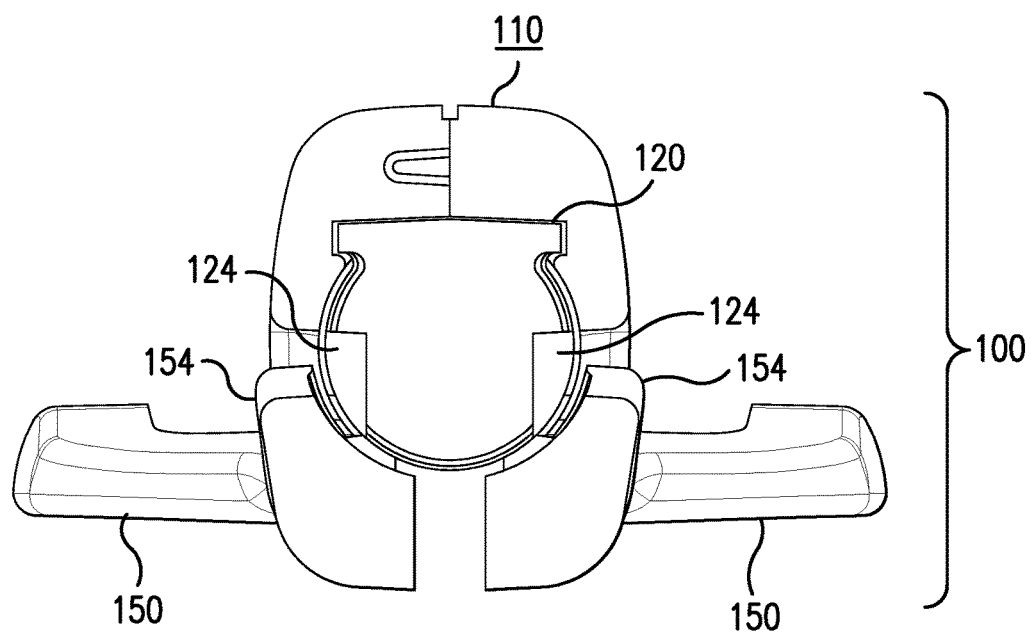
FIGS. 5B and 5C are sliced views of a needle holder and introducer in accordance with an embodiment of the present invention.
Figure 5C:
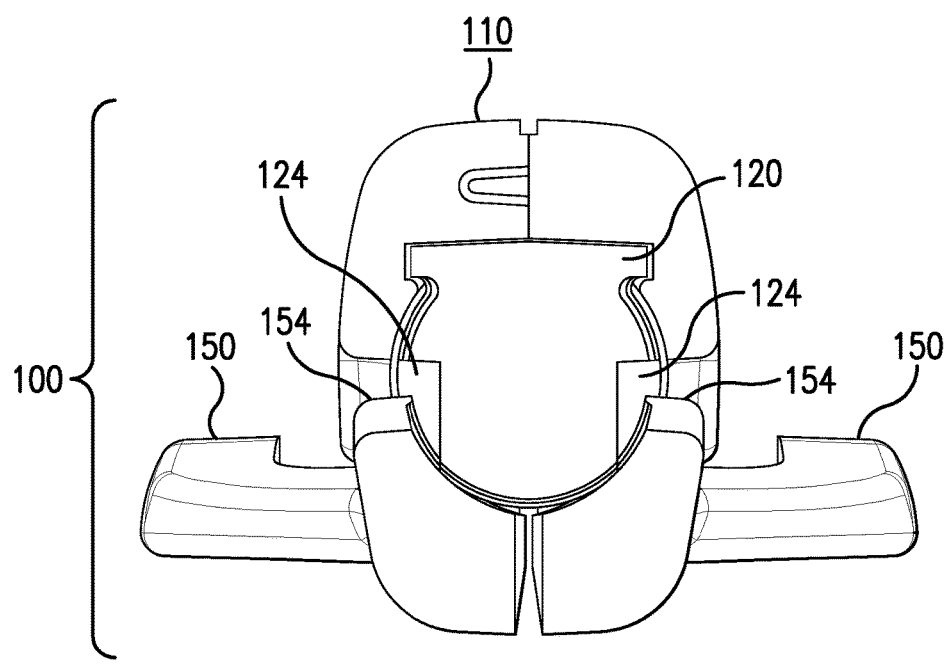

FIGS. 5A-C show close-up views of an embodiment of the needle holder 120. As can be seen in FIG. 5A, the needle holder may contain indentations 124 or other features that interact with the one or more locks of the mating components on the housing of the introducer. In the particular embodiment shown in FIG. 5A, the needle is not shown, but can be attached or otherwise connected to the needle holder 120 at its base 126. It is envisioned that other configurations could be created where the needle is not at the base of the needle holder. For example, the needle could be attached higher up. In further embodiments, the needle is permanently attached to the needle holder 120 through glue or other adhesive, being molded into the housing, or other means. Alternatively, the needle may be removable from the needle holder 120 so that a needle can be replaced or substituted.

FIGS. 5B and 5C show the cross view of the needle holder 120 in the housing 110 and interacting with the mating components 150. In FIG. 5C, the mating components 150 are holding the needle holder 120 by use of the locks 154. The locks 154 interact with the indentations 124 to prevent the needle holder 120 from moving in the needle cover (not shown), which in this embodiment is an internal cavity of the housing 110. Preferably, the configuration as shown in FIG. 5C occurs when the introducer 100 is connected to the sensor hub (not shown). In FIG. 5B, the mating components 150 have been released from the sensor hub, or otherwise released, so that the locks 154 release the indentations 124, allowing the needle holder 120 to move in the needle cover. Where a spring or other means of movement is attached to the needle holder 120, the needle holder 120 moves in the needle cover to a location in which the needle is covered.

Figure 6C:
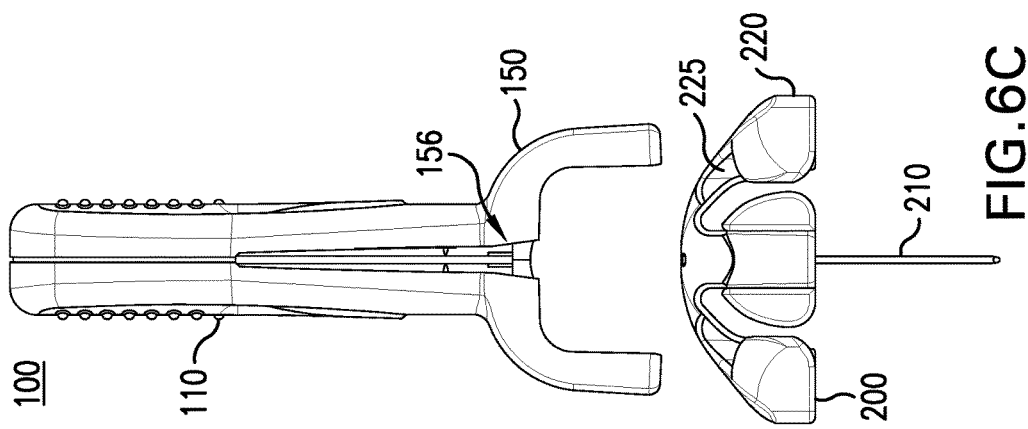
FIGS. 6A-C are views of a sensor hub and introducer in accordance with an embodiment of the present invention.
Figure 6B:
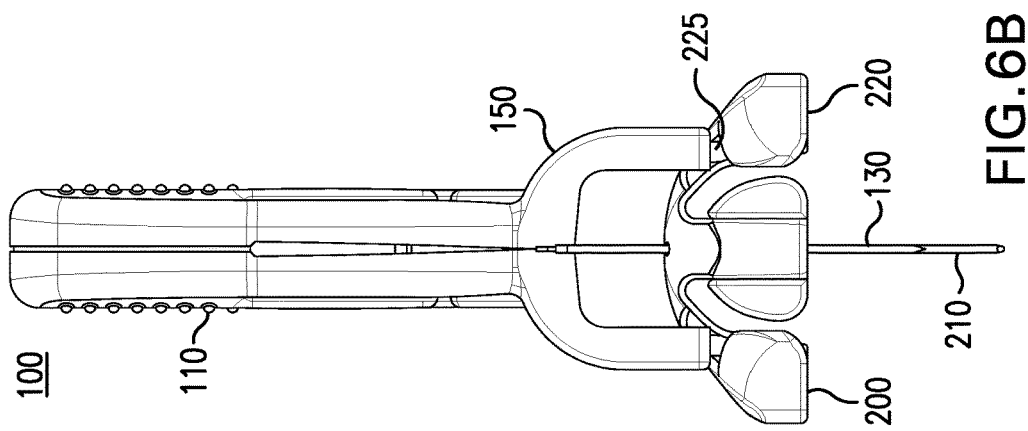
Figure 6A:
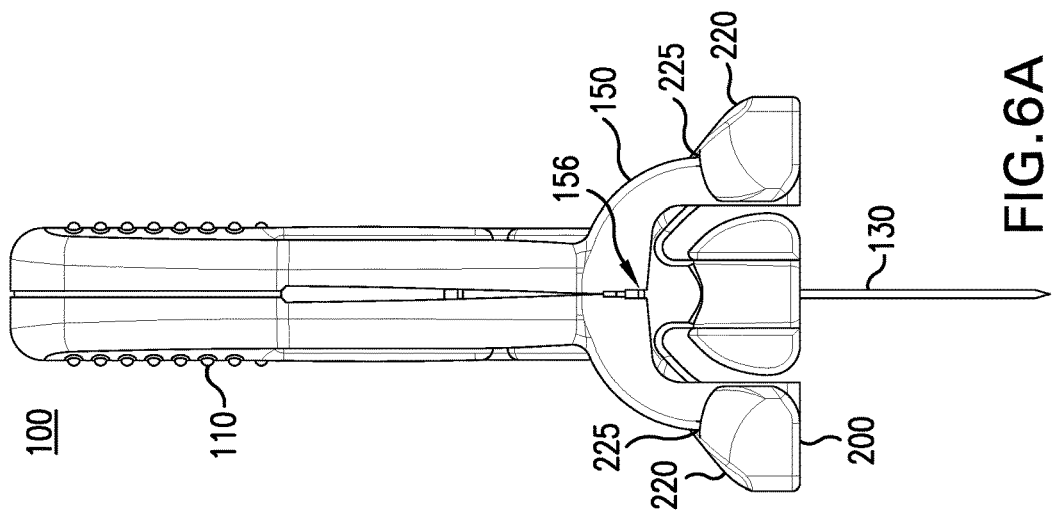

FIGS. 6A-C show the introducer 100 in combination with the sensor hub 200. In FIG. 6A, the introducer 100 is connected to the sensor hub 200. The mating components 150 are held by cavities 225 in the sensor hub arms 220. The cavities 225 may be shaped concavely or otherwise to conform to the shape of the mating components 150. In preferred embodiments, when the introducer 100 is connected to the sensor hub 200 the mating components 150 are held towards each other so that their edges 156 are close to each other. This keeps the locks (154 in FIGS. 5A-C) interacting with the indentations (124 in FIGS. 5A-C) to prevent movement of the needle holder and keeping the needle 130 extended. FIG. 6B shows the movement of the introducer 100 away from the sensor hub 200. As can be seen, the mating components 150 are just about to be released from the cavities 225 in the sensor hub arms 220. Thus, the mating components 150 are still held towards each other and the needle 130 is still extended. The sensor 210 is visible as well, because the entire introducer has been moved up in relation to the sensor hub 200, including the needle 130. Finally, FIG. 6C shows the introducer 100 after being disconnected from the sensor hub 200. The mating components 150 are separated from the cavities 225 in the sensor hub arms 220. Thus, the mating components 150 are no longer held together and their edges 156 are separated slightly (in this embodiment by about 3 degrees per side of deflection from their initial position), which allows the locks of the mating components and the indentations of the needle holder to release. The needle holder can thereby move in the housing 110 of the introducer 100. The needle is no longer visible, because it has moved into the needle cover in the housing 110.

Figure 7:
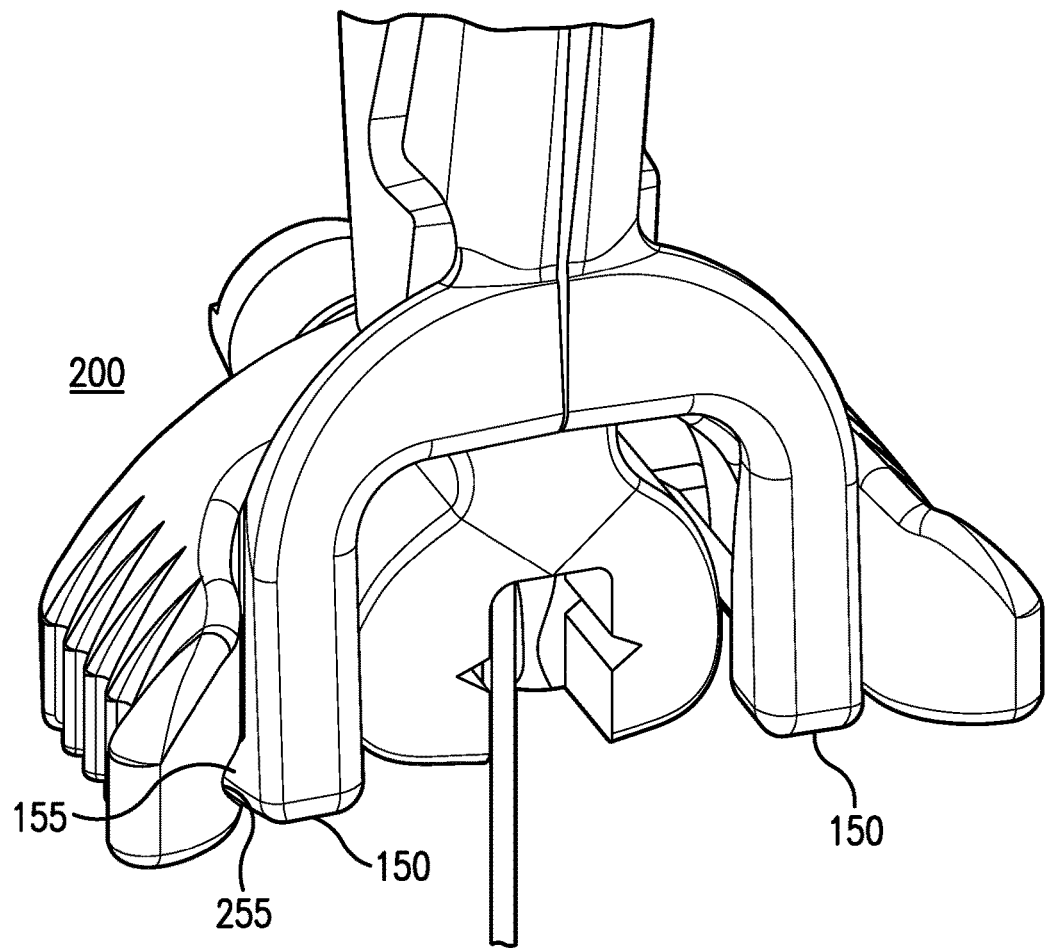
FIG. 7 is a partial view of a sensor hub and introducer in accordance with an embodiment of the present invention.

The mating components may hold the introducer in connection with the sensor hub through friction. The combination of the mating of the mating components with the matching cavities on the sensor hub and the force pushing the mating components away from each other (discussed above) creates a friction that keeps the introducer and sensor hub together. A user need only pull the introducer up to separate the introducer from the sensor hub. In FIG. 7, a catch 155 is shown on one of the introducer mating components 150 that would interact with a matching recess 255 in the sensor hub 200 to provide additional stability when the introducer 100 is connected to the sensor hub 200. With a small catch like that shown in FIG. 7, it would still be possible for a user to separate the introducer from the sensor hub 200 by pulling the two components away from each other. In alternative embodiments, the catch could be on the sensor hub and the recess could be on the mating component. There may be multiple catches and recesses, for example one catch or recess on each mating component or multiple catches/recesses on each mating component. There may be any other type of mechanism to lock the introducer 100 and sensor hub together. As an example, there may be a mechanism that needs to be released, such as by pressing a button or removing a hook. In alternative embodiments, the mechanism may be an adhesive, weld or the like.

Figure 8:
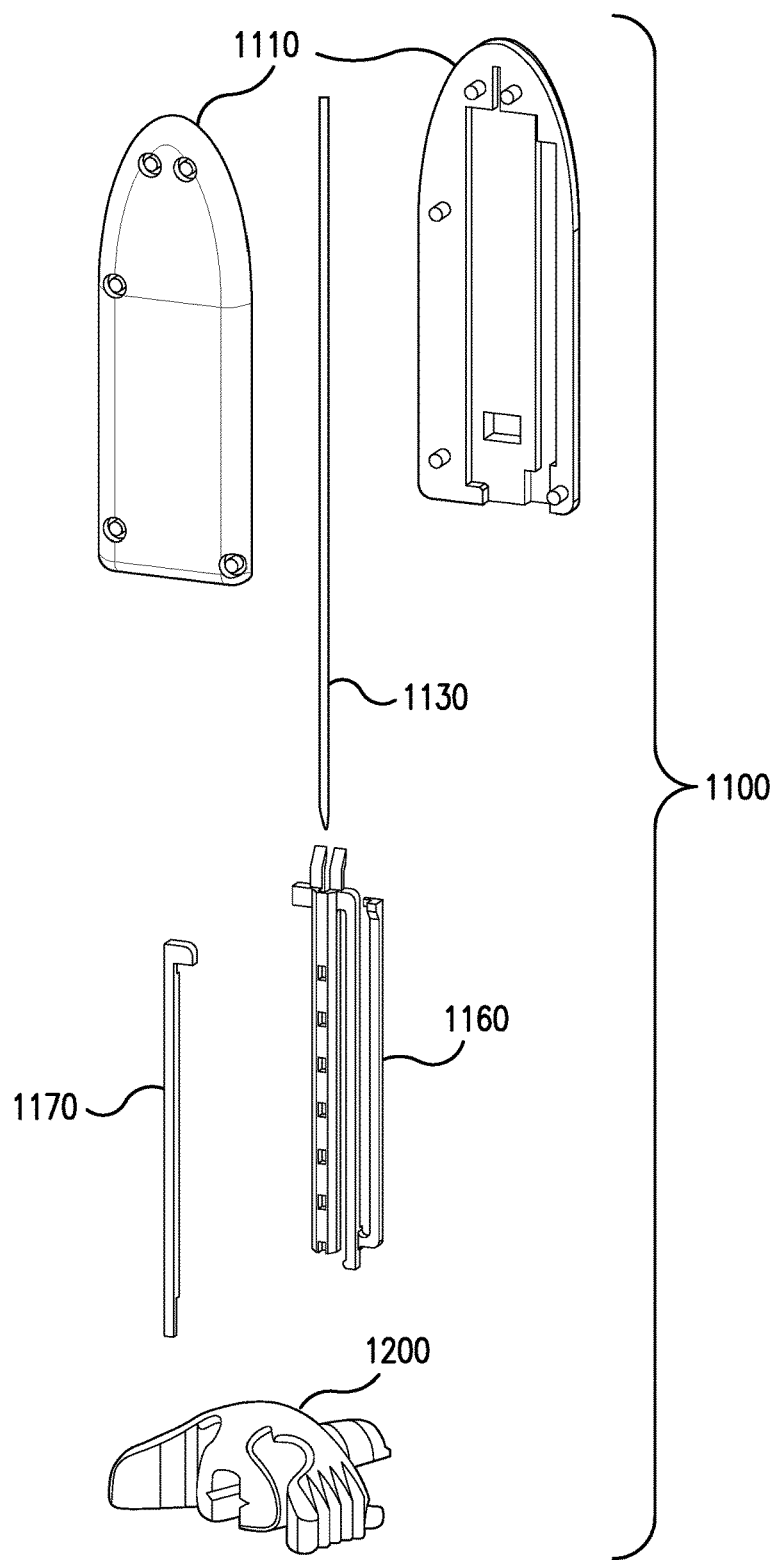
FIG. 8 is an expanded view of an introducer and sensor hub in accordance with an embodiment of the present invention.

A second embodiment of an introducer in accordance with the present invention is shown in FIG. 8. The introducer 1100 includes a housing 1110, needle 1130, and needle cover 1160, which includes a locking element 1170. The introducer 1100 is connectable to a sensor hub 1200. The needle cover 1160 can extend from the housing 1110 to cover the needle 1130. In this embodiment, it is preferred that the needle 1130 is connected to the housing 1110 so that it does not move with relation to the housing 1110. Instead, the needle cover 1160 extends over the needle 1130. Thus, like the embodiment discussed above, the needle cover 1160 moves in relation to the needle 1130 such that the needle may be covered by the needle housing. In further embodiments, a combination of the two embodiments discussed herein could be used, where the needle moves at least partially into the housing so that it is partially covered by an interior cavity of the housing and a needle cover extends out of the housing to cover the remaining part of the needle that is still extending from the housing.

FIG. 9A shows an exterior view of the introducer 1100 prior to using the introducer to introduce a sensor. The sensor hub is not shown in this figure. The needle 1130 extends out of the housing 1110. The needle cover 1160 is substantially contained within the housing 1110, although in the embodiment pictures, a small portion of the needle cover 1160 extends that interacts with the sensor hub. In further embodiments, the sensor hub could have an extension that would extend slightly into the housing 1110 when the introducer 1100 is connected to the sensor hub, so that the needle cover 1160 could be entirely within the housing 1100. FIG. 10A shows the same introducer 1100 as in FIG. 9A, but in a cut-away view. As can be seen, the needle cover 1160 is substantially contained within the housing 1110. The needle 1130 is attached to the housing 1110 at 1115. This attachment can be achieved through glue or other adhesive or through molding or any other desired means.

FIG. 9B shows the introducer 1100 after use as an introducer is complete. For example, the introducer 1100 was used to insert a sensor on a sensor hub and now has been separated from the sensor hub. The needle cover 1160 now substantially extends out of the housing 1110, covering the needle so that it is hidden. In the embodiment shown in FIG. 9B, the needle is substantially covered, although there are small holes in the cover through which the needle can be seen. The portion of the needle extending from the housing 1110 is covered by the needle cover 1160. The remainder of the needle is covered within the housing 1110. In alternative embodiments, the needle cover completely covers the needle. In still further embodiments, the needle cover may cover less of the needle, but the tip is preferably covered to prevent injury. FIG. 10B shows the same introducer 1100 as FIG. 9B, but in a cut-away view. As can be seen, the needle cover 1160 is extended out of the housing over the needle 1130 such that the needle 1130 is substantially covered.

Figure 11E:
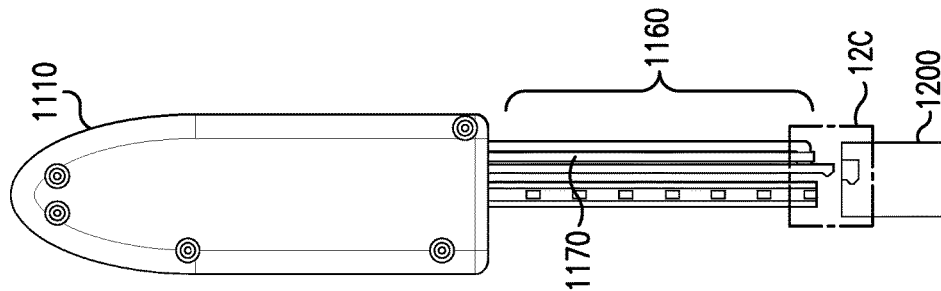
FIGS. 11A-E are views of an introducer and block representative of a sensor hub in accordance with an embodiment of the present invention.
Figure 11D:
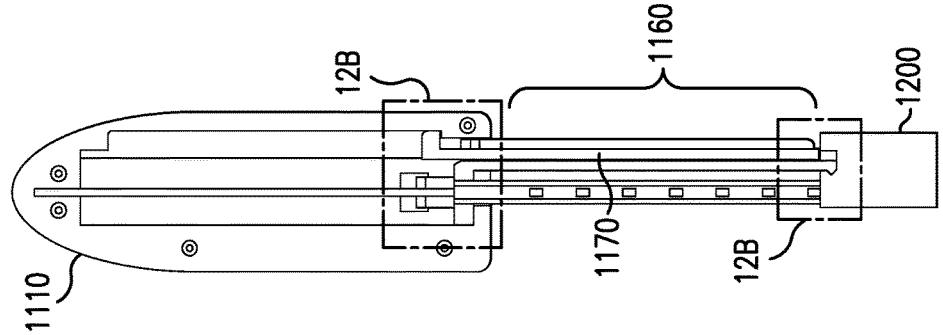
Figure 11C:
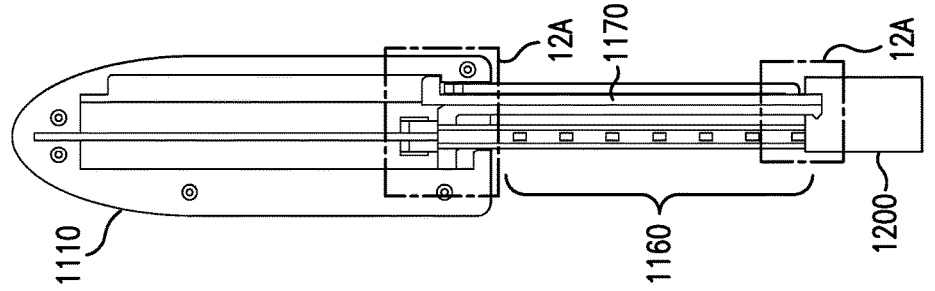
Figure 11B:
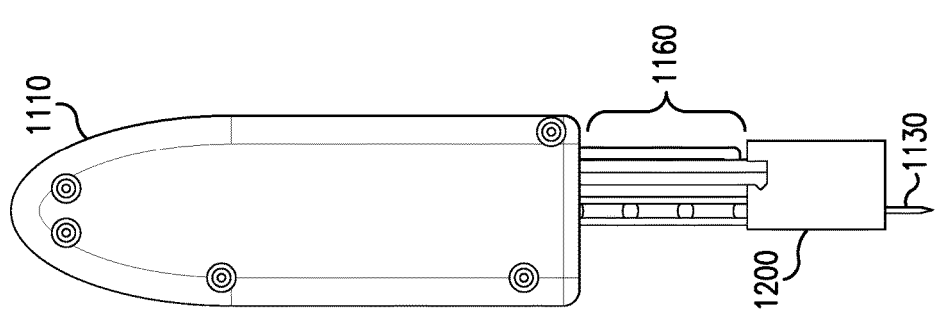
Figure 11A:
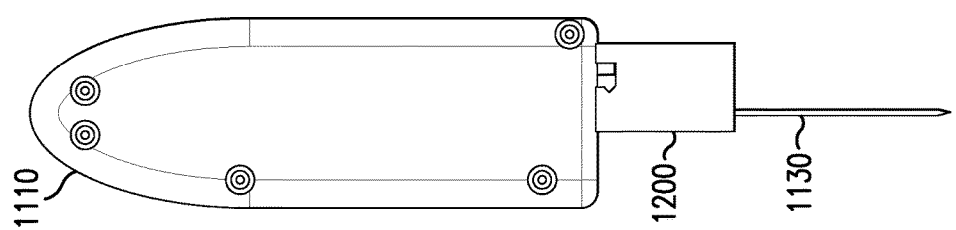
Figure 12A:
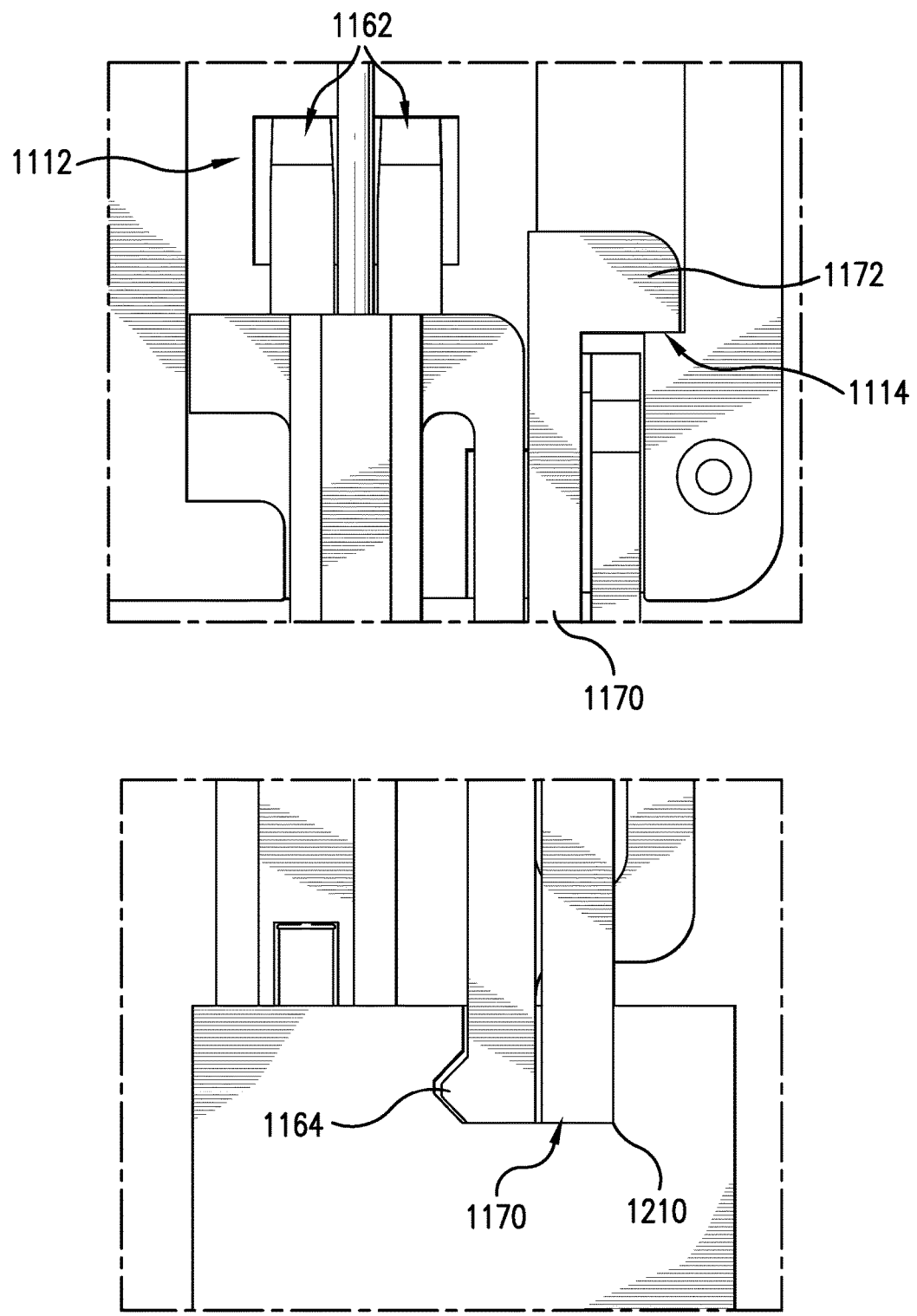
FIGS. 12A-C are close-up views of portions of FIGS. 11C-D in accordance with an embodiment of the present invention.
Figure 12B:
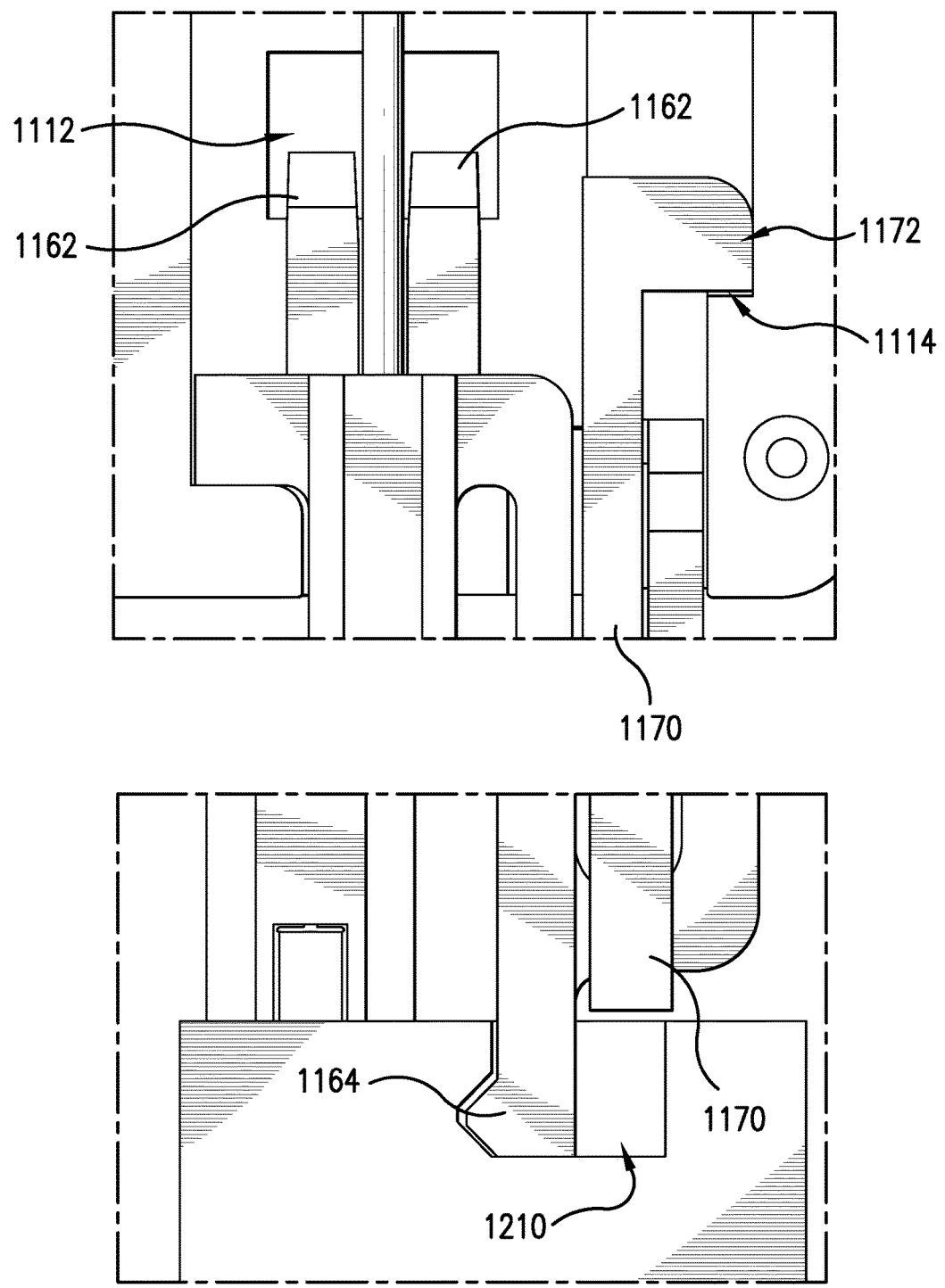
Figure 12C:
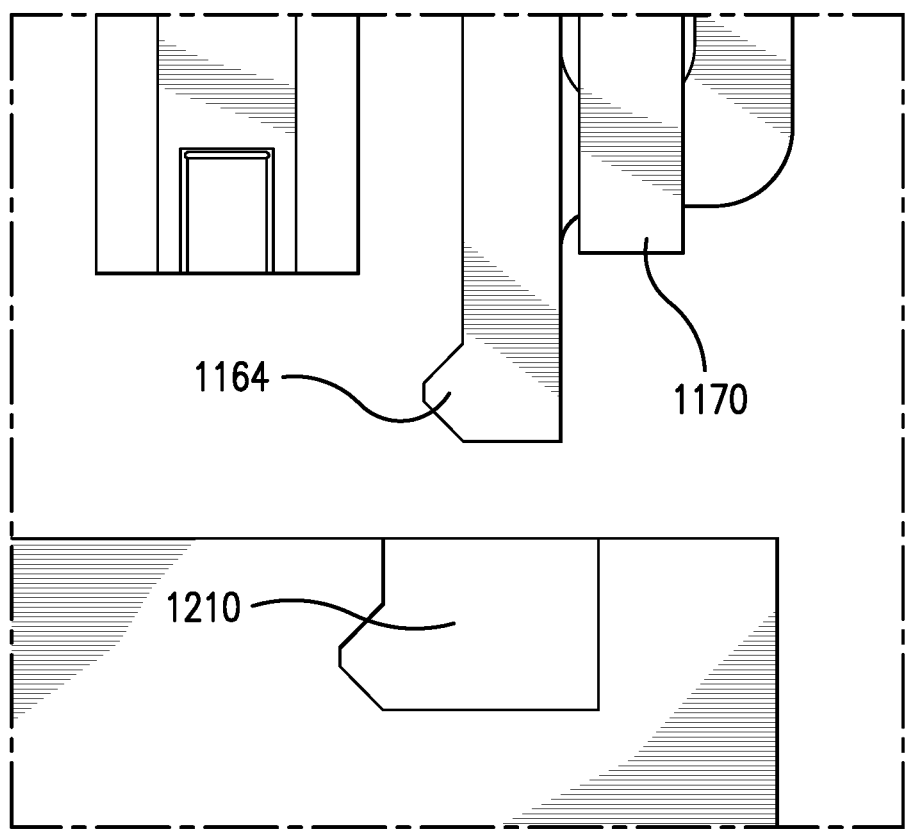

FIGS. 11A-E show the introducer 1100 and a box representing a sensor hub 1200 in various stages of the present invention. The sensor is not shown but would preferably be extending out of the sensor hub in the same direction as the needle. FIGS. 12A-C show close-up views of the boxed areas of FIGS. 11C-E, respectively. In FIG. 11A, the sensor hub 1200 is connected to the introducer 1100 and the needle 1130 is exposed so that a sensor may be introduced into a patient. The needle cover is substantially contained in the housing 1100. As shown in FIG. 11B, the housing is separated from the sensor hub 1200 by pulling the two components away from each other. The needle 1130 is still partially exposed. The pulling of the housing 1110 away from the sensor hub 1200 causes the needle cover 1160 to extend out of the housing. FIG. 11C shows the sensor hub extended from the housing 1110 of the introducer 1100. As can be seen, the needle cover 1160 is almost completely extended. The needle cover 1160 includes the locking element 1170. In the close-up view shown in 12A, the locking element 1170 includes a locking element catch 1172 that catches on an internal locking ledge 1114 of the housing 1110. The needle cover 1160 includes two locks 1162 that interact with an opening 1112 to lock the needle cover 1160 in an extended position for covering the needle. When the locks 1162 are engaged in the opening 1112, they catch on the opening. In the embodiment shown in FIG. 11C, the locks bend into the opening when the needle cover moves over the needle. The locks and opening then prevent the needle cover from moving back into the housing. Other suitable mechanisms for keeping the needle cover extended may also be used.

The needle cover 1160 also includes a needle cover catch 1164 that catches on the sensor hub 1200 in a cavity 1210 to allow the needle cover 1160 to extend when the sensor hub 1200 is being drawn away from the housing 1110. When the locking element 1170 remains in the cavity 1210, the needle cover catch 1164 cannot disengage from the cavity 1210, which causes the locking element 1170 to extend from the housing 1110. As shown in FIGS. 11D and 12B, the locking element catch 1172 has caught onto the internal locking ledge 1114 to move the locking element 1170 with respect to the rest of the needle cover 1160. When the locking element 1170 moves, it comes out of the needle cover cavity 1210. This allows the locking element catch 1164 to move in the cavity 1210 and then detach from the cavity 1210, because it is no longer blocked by the locking element 1170. The needle cover 1160 can then disconnect from the sensor hub 1200. FIG. 11E shows the introducer 1100 detached from the sensor hub 1200 and the needle cover 1160 covering the needle. FIG. 12C is a close-up view showing the needle cover catch 1164 and locking element 1170 separated from the cavity 1210. Once the needle is covered, the introducer can be disposed of without risking harm to the user.

Figure 13A:
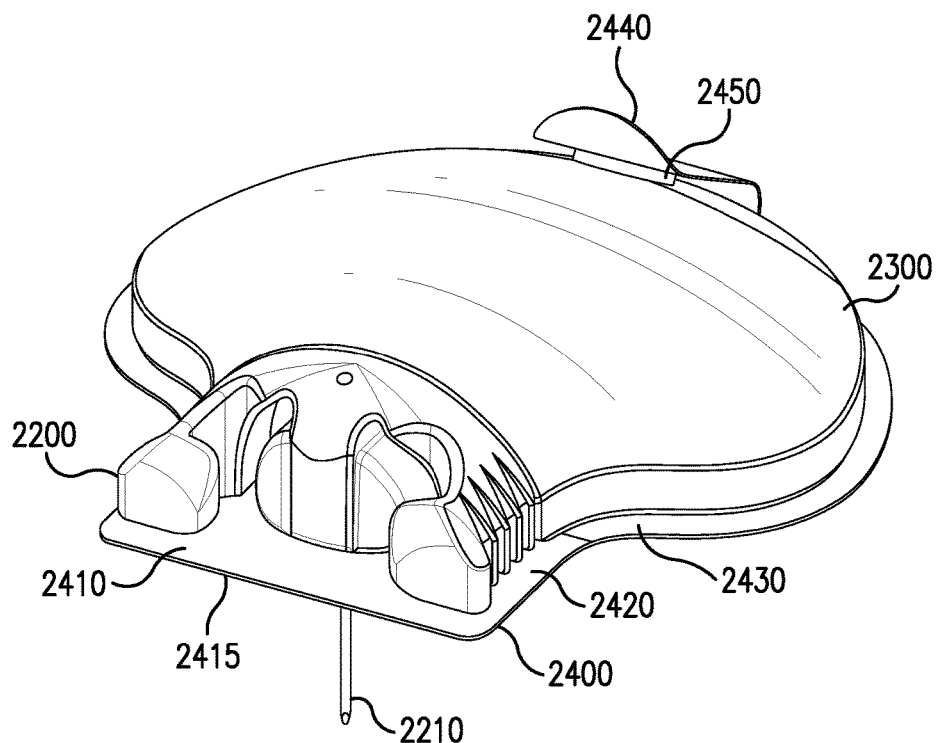
FIG. 13A is a view of a sensor hub, sensor electronics hub, and mounting base in accordance with an embodiment of the present invention.

Sensor sets are also contemplated that include the introducer described above, a sensor hub, and sensor electronics. A sensor hub 2200 and sensor electronics 2300 according to the invention are shown in FIG. 13A. Additional sensor hubs and sensor electronics are shown in co-owned, pending application Ser. No. 12/056,651, filed Mar. 27, 2008, and Ser. No. 11/322,568, filed Dec. 30, 2005. Sensor electronics may be directly connected to the sensor hub, or connected via a wire or other means to the sensor hub. When sensor electronics and sensor hubs are intended to be attached to a patient via a mounting base, if only the sensor hub is attached to the mounting base, the sensor electronics can pull away or wobble, causing discomfort and concern that the entire set might fall off of the patient. In preferred embodiments, the mounting base has a relatively flat shape. In one embodiment, the entire mounting base is about the thickness of a penny. The mounting base may be made out of a flexible and breathable material. For example, the mounting base may comprise cloth, band-aid-like material, and the like. Such materials may allow the patient more comfort. The adhesive layer may make it easy to affix or remove the sensor. In further embodiments, the mounting base is configured to be in a slim configuration so that it can fit closer against the patient's body when worn. The slim shape provides more comfort while being less conspicuous, for example, when worn under clothes. Further types of mounting bases can be seen in commonly assigned pending application Ser. No. 11/234,722 filed on Sep. 23, 2005.

The mounting base may be made of materials such as cloth, band-aid-like material, and the like. For example, materials could include polyurethane, polyethylene, polyester, polypropylene, PTFE, or other polymers. These could be woven, knitted, non-woven, molded, or extruded, for example. Additionally, the material may be flesh-colored to provide more discreteness. In preferred embodiments, the mounting base is shaped to closely mimic the shape of the sensor hub connected to the sensor electronics hub to minimize the amount of contact necessary with the skin while blocking the sensor hub or sensor electronics hub from contacting the skin, thus minimizing allergic reaction. The mounting base may be other shapes, such as circular, oval, hour-glass, butterfly or the like.

As shown in FIG. 13A, in one embodiment, a mounting base 2400 is provided. The mounting base contains a first side 2410 and a second side 2415. The first side 2410 is adapted to be attached to the sensor hub 2200 and sensor electronics hub 2300. The second side 2415 is adapted to be attached to the skin of a patient using an adhesive that is sufficiently long-lasting to allow the mounting base to stay on the patient's skin for at least 3 days, but removable in that the patient can remove the mounting base from the skin when desired. While the adhesive on the second side 2415 does not need to be reusable, because the sensor hub 2200 would generally be used only once, it is envisioned that it could be a reusable adhesive. In alternative embodiments, the adhesive may adhere for 5 days, 6 days, 7 days, 8 days, or more, with the length being dependent on the life of the sensor and the needs of the patients. In further alternative embodiments, the adhesive may include an antimicrobial, such as silver, anti-biotics, dexamethasome or the like, to reduce the chance of infections during use.

Figure 13B:
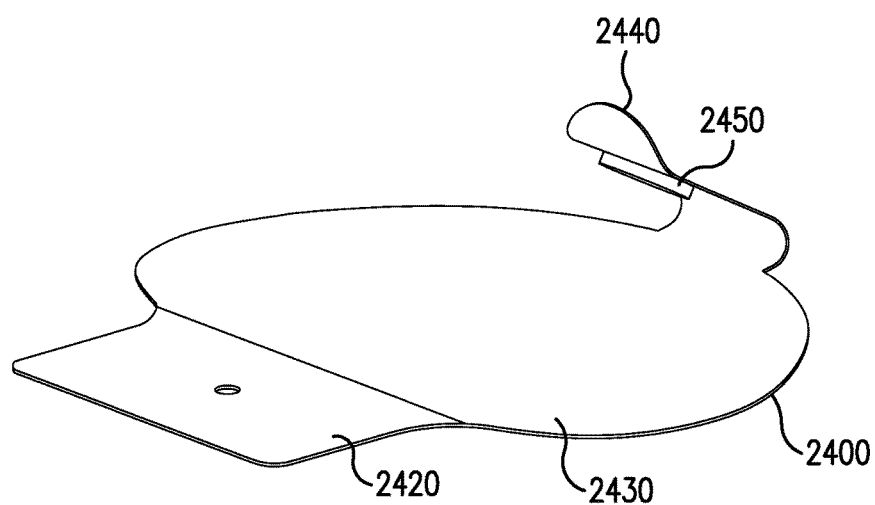
FIG. 13B is a view of the mounting base of FIG. 13A in accordance with an embodiment of the present invention.
Figure 14A:
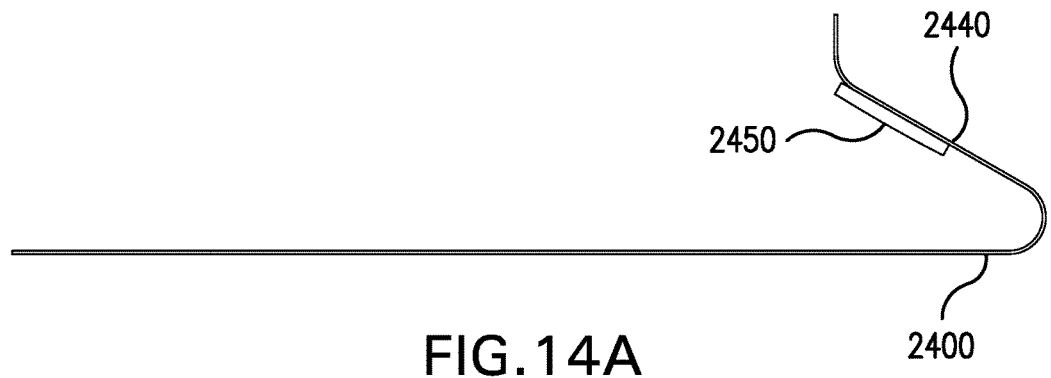
FIG. 14A is a side view of a mounting base in accordance with an embodiment of the present invention.
Figure 14B:
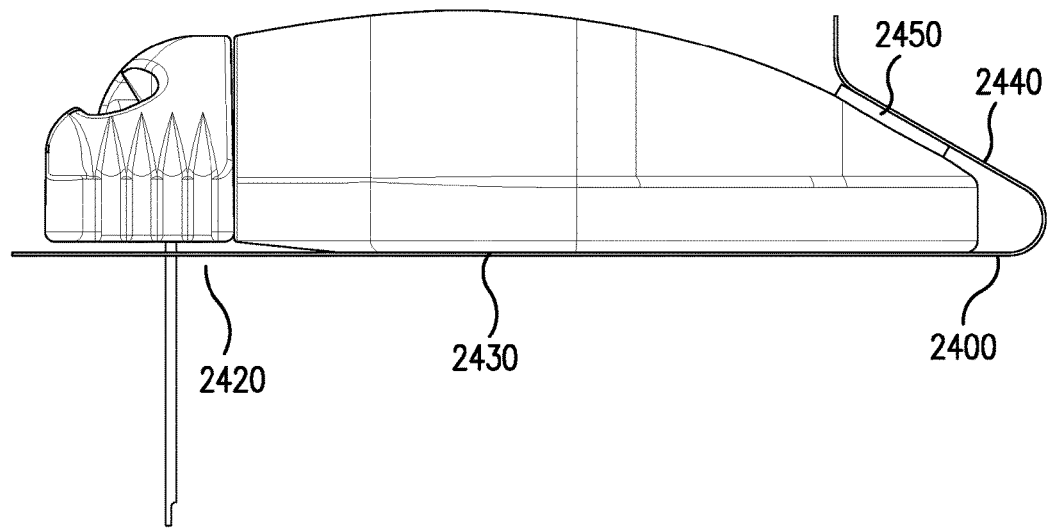
FIG. 14B is a side view of a mounting base, sensor hub and sensor electronics hub in accordance with an embodiment of the present invention.
Figure 15:
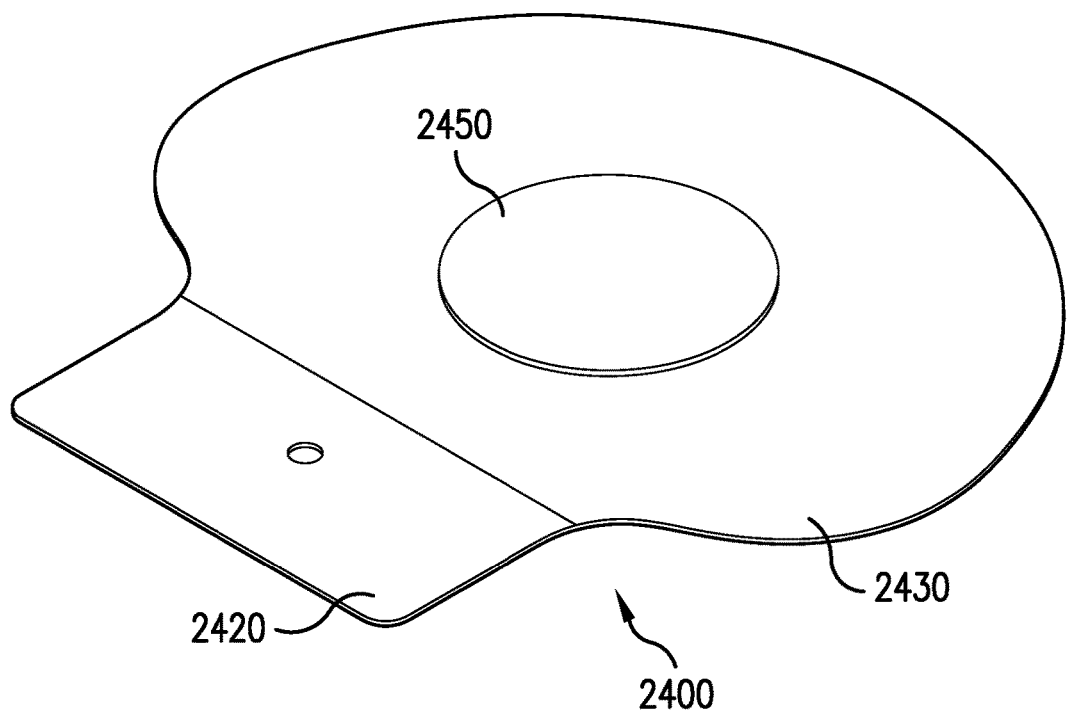
FIG. 15 is a view of a mounting base in accordance with an embodiment of the present invention.

The first side 2410 of the mounting base 2400 contains a first base portion 2420 and a second base portion 2430. The sensor hub 2200 is attached to the first base portion 2420, preferably in a permanent manner. However, in alternative embodiments, a non-permanent adhesive could be used. The second base portion 2430 is adapted to mate with the sensor electronics hub 2300. There does not need to be any adhesive on the underside of the sensor electronics hub 2300 or on the portion of the second base portion 2430 directly underneath the sensor electronics hub 2300. In the embodiment shown in FIGS. 13A-B, the second base portion 2430 contains a mounting extension 2440 configured to extend to the top of the sensor electronics hub 2300. This would allow easy insertion and removal from the sensor without the transmitter getting stuck during these operations. A reusable adhesive 2450 is attached to the second base portion 2430 at the mounting extension 2440. Additional mounting extensions with reusable adhesive could also be used to create additional security. As an alternative, the second base portion could include a pocket that fits around at least a portion of the sensor electronics hub, and the reusable adhesive could be within that pocket. The reusable adhesive 2450 removably adheres to the sensor electronics hub 2300 so that the sensor electronics hub 2300 can be removed from the mounting base 2400. FIGS. 14A and 14B show the same embodiment of FIGS. 13A and 13B but from a side view. In FIG. 15, there are no mounting extensions. The reusable adhesive 2450 is on the second base portion directly under the sensor electronics hub, keeping a more streamlined look.

While a sensor hub is generally used only once, a sensor electronics hub is usually reusable. The sensor electronics hub contains the electronics necessary to read signals from the sensor 2210. The electronics are usually expensive enough that they should be used for more than the few days of a sensor lifetime. Thus, a sensor electronics hub is usually made to connect to multiple sensor hubs. In addition, a sensor electronics hub may need to be recharged or inserted into a docking station for any number of reasons. The user may want to keep the same sensor on while the recharging or docking happens. As such, being able to detach the sensor electronics hub from the sensor hub and mounting base is desirable.

In a preferred embodiment, the sensor electronics hub 2300 is substantially stationary with respect to the second base portion 2430 when it is attached with the reusable adhesive. The reusable adhesive is a suitable adhesive that can be reused a number of times. Suitable adhesives could consist of silicone, rubber, natural rubber, and/or acrylic. For example, commercial adhesives could include 3M™ adhesive 300 series (acrylic); 3M™ adhesive 800 series (natural rubber); 3M™ adhesive 700 series (synthetic rubber); and 3M™ silicone adhesive. The adhesives may be pressure sensitive adhesives.

In preferred embodiments, the sensor electronics hub includes a wireless transmitter to transmit information from the sensor electronics hub to a computer, user interface, or infusion pump. The wireless transmitter may be part of a transceiver or may be used in conjunction with a receiver.

The mounting base described herein may be used in conjunction with the other embodiments discussed herein or with any other sensor set as may be desired.

In further embodiments, there is provided a sensor hub that hides the introducer needle from the user by either having a sliding mechanism or having the needle partially over the sensor tube prior to insertion in a pre-insertion position. Both embodiments may or may not be used with a needle protection device that would retract or cover the needle after insertion of the sensor has occurred. Some patients do not like to see a needle before it is used to introduce a sensor or cannula into their body. By hiding the needle within the sensor hub, this allows the user to not have to see the needle. Instead, the user would just feel the needle insertion when the needle is inserted into the body.

Figure 16A:
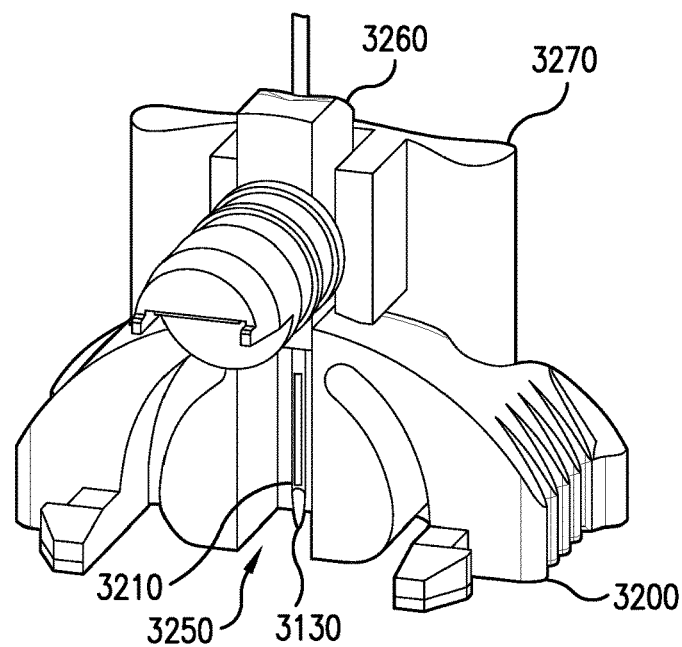
FIGS. 16A and 16B are views of a sensor hub in accordance with an embodiment of the present invention.
Figure 16B:
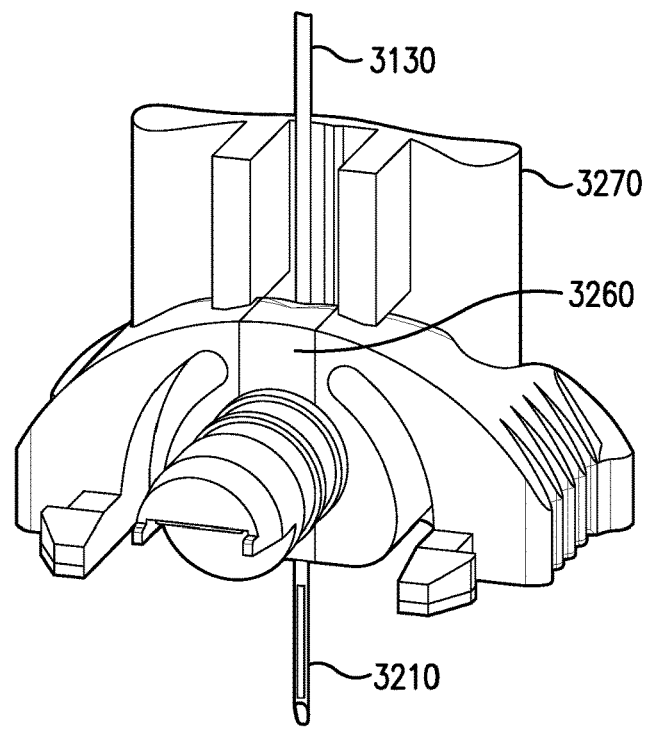

In FIG. 16A, the sensor hub 3270 has a base 3200 and a sensor carrier 3260. The base 3200 has a pocket 3250 in which is hidden the needle 3130 and sensor 3210 prior to use when the sensor hub 3270 is in a pre-insertion position. There may or may not be a third piece, a guide which guides the sensor carrier 3260 into the final position, an insertion position (during and/or after insertion). During use, the force applied to the bottom of the base 3200 due to the interaction with the users' body would cause the sensor carrier 3260 to collapse into position; this action would insert the needle 3130 and sensor 3210 into the body. FIG. 16B shows the position of the sensor hub 3270 after the sensor carrier 3260 has slid into the pocket 3250.

Figure 17A:
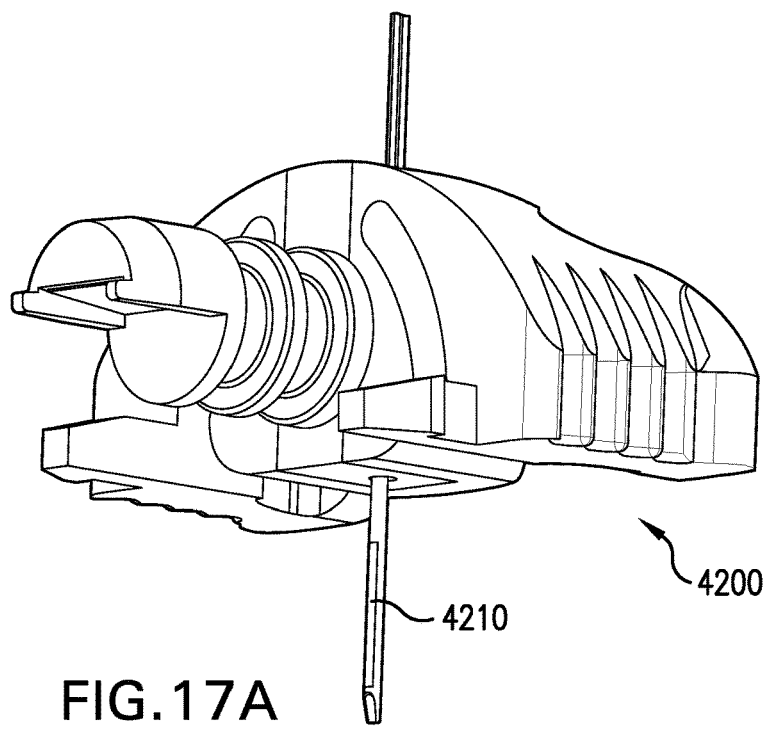
FIGS. 17A and 17B are views of a sensor hub in accordance with an embodiment of the present invention.
Figure 17B:
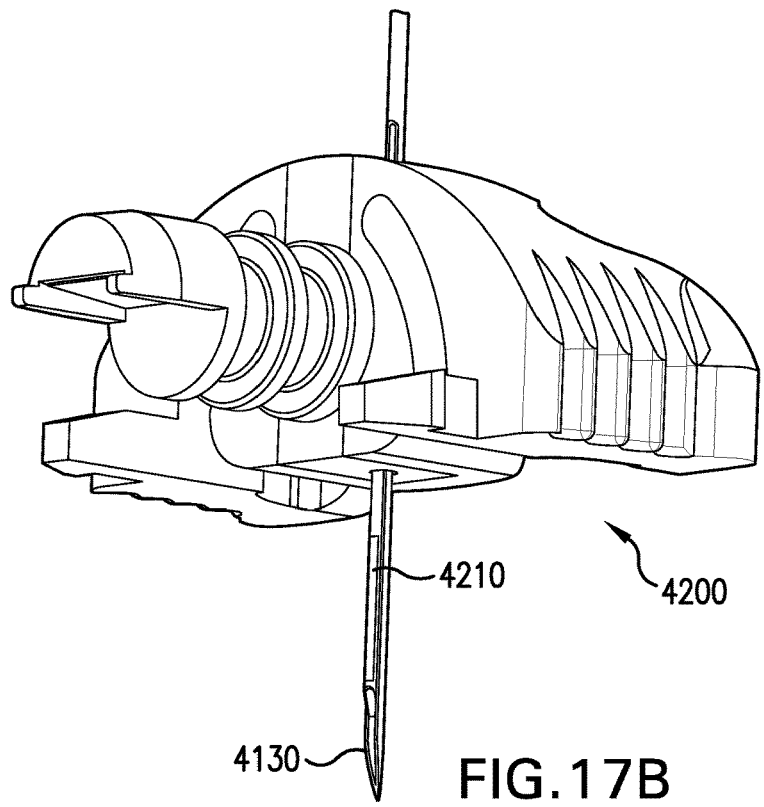

FIGS. 17A and 17B show another embodiment of a sensor hub 4200 in which a needle 4130 is hidden prior to use in a pre-insertion position. As shown in FIG. 17A, only the sensor 4210 is visible. The sensor needle 4130 would be partially engaged with the sensor tube prior to insertion. A feature on an inserting device (not shown) would engage the sensor 4210 entirely with the needle 4130 for insertion in an insertion position.

In alternative embodiments, the introducers disclosed herein may be used with infusion sets for infusing a therapeutic substance, such as insulin, into the body of a patient. Generally, infusion sets include a cannula housing with a cannula that is inserted into the body of a patient with the assistance of a needle. The introducers described herein could work with cannula housings that are structured to interact in the same way as the sensor hubs described above. Infusion sets and other introducers for infusion sets are described in, for example, U.S. Pat. Nos. 6,759,589, 5,522, 803, 5,986,011, 6,086,575, 6,123,690, 6,335,021, 6,736,797, 6,302,866, 6,949,094, 7,303,543, 6,520,938, 6,056,718, and 5,851,197, 7,303,548 which are herein incorporated by reference and commonly assigned pending U.S. patent application Ser. No. 11/050,101, filed Feb. 3, 2005 and Ser. No. 11/058,074, filed Feb. 15, 2005, which are herein incorporated by reference.

The sensor hubs and introducers described herein can be made of any substantially rigid plastic. For example, they may be made from a suitable plastics material that is substantially rigid but will allow it to flex and bend, such as polypropylene. However, the introducer may also be made out of a non-flexible material, such as polycarbonate, if preferred. Alternatively, the introducer may be made out of any suitable flexible or non-flexible material such as polyethylene, polyurethane, polyvinyl chloride, resins, polymers, ceramics, composites, or the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of covering an introducer needle comprising:
providing a sensor hub, a sensor, and an introducer, the introducer being configured to insert the sensor into a patient, the introducer comprising:
a housing detachably connectable to the sensor hub, wherein the sensor hub contains the sensor prior to connection to the housing, the housing including a needle cover, wherein the needle cover is an internal compartment of the housing;
a needle that is moveable with respect to the needle cover and is extendable out of, and retractable into, the housing;
a needle holder connected to the needle and contained within the housing; and
a spring having a top end in contact with the needle holder and a bottom end in contact with the housing,
wherein said needle holder and spring are configured such that, when the housing is connected to the sensor hub, said spring is in a compressed position and the needle extends out of the housing to insert the sensor into the patient, and such that disconnection of the housing from the sensor hub causes said spring to expand, thereby retracting the needle into the housing to be covered by said needle cover inside the housing, and the sensor remaining inserted in the patient;
wherein the housing includes a mating component to mate with the sensor hub and hold said spring in said compressed position when the housing is connected to the sensor hub; and
wherein the mating component includes a lock that locks the needle holder into a needle extended position when the housing is connected to the sensor hub, and when the mating component is not mated with the sensor hub the housing is completely detached from the sensor hub;
connecting the housing to the sensor hub so as to insert the sensor into the patient; and disconnecting the housing from the sensor hub, whereby the needle cover covers the needle when the housing is detached from the sensor hub.

2. The method of claim 1, wherein the needle holder is slidably coupled to the housing.

3. The method of claim 1, wherein the housing and the mating component are configured such that disconnection of the housing from the sensor hub causes the mating component to release the needle holder such that the needle holder may move the needle to be covered.

4. The method of claim 1, wherein the mating component is held in a locking position by friction when the housing is connected to the sensor hub.

5. The method of claim 1, wherein the mating component includes a catch that catches on the sensor hub when the housing is connected to the sensor hub, whereby the mating component is held in a locking position by the catch.

6. The method of claim 1, wherein the needle is permanently covered by the needle cover after the housing is disconnected from the sensor hub.

7. The method of claim 1, wherein the needle holder has a top portion that defines an indentation therein, said indentation extending radially inwards from a periphery of said top portion, and wherein, when the housing is connected to the sensor hub, said lock extends into, and engages with, said indentation on the needle holder's top portion, thereby locking the needle holder in the needle extended position.

8. The method of claim 1, wherein the needle holder has a top portion that defines two indentations therein, wherein the housing includes a second mating component, wherein said second mating component includes a second lock, and wherein, when the housing is connected to the sensor hub, each said lock extends into, and engages with, a respective one of said indentations, thereby locking the needle holder in the needle extended position.

9. The method of claim 8, wherein each said mating component includes an arm, and wherein the arms are moveable towards, and away from, each other.

10. The method of claim 9, wherein, when the arms are moved towards one another, each said lock extends into, and engages with, a respective one of said indentations on the needle holder's top portion, and when the arms are moved away from one another, each said lock disengages from each said respective indentation.

* * * * *